(12) United States Patent
Koyama et al.

(10) Patent No.: US 8,277,421 B2
(45) Date of Patent: Oct. 2, 2012

(54) DRUG SOLUTION INJECTOR

(75) Inventors: Shingo Koyama, Yamanashi-ken (JP);
Masafumi Takemoto, Yamanashi-ken (JP); Hiromitsu Okabe, Tokyo (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 214 days.

(21) Appl. No.: 12/670,218

(22) PCT Filed: Oct. 31, 2007

(86) PCT No.: PCT/JP2007/071249
§ 371 (c)(1),
(2), (4) Date: Mar. 11, 2010

(87) PCT Pub. No.: WO2009/013844
PCT Pub. Date: Jan. 29, 2009

(65) Prior Publication Data
US 2010/0198151 A1    Aug. 5, 2010

(30) Foreign Application Priority Data
Jul. 23, 2007  (JP) ................................. 2007-191469

(51) Int. Cl.
*A61M 5/32*  (2006.01)

(52) U.S. Cl. ....................................... 604/192
(58) Field of Classification Search .............. 604/110
See application file for complete search history.

(56) References Cited

U.S. PATENT DOCUMENTS
5,104,378 A * 4/1992 Haber et al. ................. 604/110
5,104,384 A * 4/1992 Parry ........................... 604/192

FOREIGN PATENT DOCUMENTS
JP   2001-070445 A   3/2001
JP   2006-255272 A   9/2006

OTHER PUBLICATIONS
International Search Report (PCT/ISA/210) issued on Dec. 4, 2007 by Japanese Patent Office as the International Searching Authority for International Application No. PCT/JP2007/071249.

* cited by examiner

*Primary Examiner* — Theodore Stigell
*Assistant Examiner* — Jason Flick
(74) *Attorney, Agent, or Firm* — Buchanan Ingersoll & Rooney PC

(57) ABSTRACT

A drug solution injector comprises a needle tube having a sharp needlepoint, a bottomed outer cylinder arranged on the base end side of the needle tube and having an inside space communicable with the inside of the needle tube, a gasket slidable within the outer cylinder, a drug solution in the space formed by the outer cylinder and the gasket, a support member supporting the needle tube and having a flow channel communicating with the inside of the needle tube, an operation mechanism permitting selection between a communicated state wherein the inside of the needle tube and the inside of the outer cylinder communicate with each other through the flow channel and a blocked state wherein the communication is blocked by rotating the support member, and an exposure preventer for preventing exposure of the needlepoint.

29 Claims, 22 Drawing Sheets

DRUG SOLUTION INJECTOR

TECHNICAL FIELD

The present invention relates to a drug solution injector.

BACKGROUND ART

Prefilled syringes which are preliminarily filled with drug solution are known. The prefilled syringe includes an outer cylinder provided with a discharge port at the distal end thereof, a gasket inserted in the outer cylinder, and a plunger (pushing element) connected to the gasket, with the drug solution contained in the space surrounded by the outer cylinder and the gasket.

At the time of injecting a drug solution into a living body by use of the prefilled syringe, a needle assembly having a hollow needle is mounted to the discharge port of the outer cylinder, and the prefilled syringe is used in this mounted state (refer to, for example, Patent Document 1). Further, in the mounted state, the inside of the outer cylinder and the inside of the hollow needle communicate with each other. The needle assembly (protective sleeve) described in Patent Document 1 includes a hollow needle, a hollow cylindrical outside member (outside sleeve member) arranged on the outer peripheral side of the hollow needle and supporting and fixing a proximal portion of the hollow needle, a hollow cylindrical inside member (inside sleeve member) disposed between the outside member and the hollow needle concentrically with the outside member and movable along the axial direction of the outside member, and a coil spring for biasing the inside member in the distal direction. In the needle assembly thus configured, the inside member may be positioned in a first state of covering the needle body up to the needlepoint or a second state of exposing the needlepoint by moving relative to the outside member along the axial direction of the outside member. In addition, by the biasing force of the coil spring, the inside member can be maintained in the first state.

In the needle assembly described in Patent Document 1, however, the inside member in the first state is brought into the second state when it is only pushed in the proximal direction against the biasing force of the coil spring. Therefore, even in the case where such a pushing force is inadvertently exerted on the inside member, the inside member is put into the second state, resulting in that a finger or the like may be punctured, by mistake, by the needlepoint exposed from the inside member. Further, in the needle assembly described in Patent Document 1, regardless of whether the needlepoint protrudes from the inside member, the drug solution would flow out through the hollow needle if only the plunger is pushed. Therefore, in the case where the plunger is pushed inadvertently, the drug solution would flow out uselessly (would be wasted), making it impossible to inject a predetermined amount of drug solution.

Patent Document 1: Japanese Patent No. 2872318

DISCLOSURE OF THE INVENTION

An object of the present invention is to provide a drug solution injector with which a needlepoint of a needle tube can be securely prevented from being exposed unintentionally and a drug solution can be assuredly prevented from being accidentally caused to flow out through the needle tube.

In order to achieve the above object, the present invention provides a drug solution injector including: a needle tube having a sharp needlepoint at a distal end thereof; an outer cylinder having a bottomed hollow cylindrical shape, the outer cylinder being located on the proximal side of the needle tube and having an inside space that can communicate with the inside of the needle tube; a gasket slidable within the outer cylinder; a drug solution contained in the space surrounded by the outer cylinder and the gasket; a support member which supports the needle tube and has a flow channel having a distal end capable of communicating with the inside of the needle tube and a proximal end capable of communicating with the inside of the outer cylinder; an operation mechanism which is fixed in a state of covering at least the needlepoint of the needle tube and performs selection of a communicating state wherein the inside of the needle tube and the inside of the outer cylinder communicate with each other through the flow channel or a blocked state wherein the communication is blocked by rotating the support member; and exposure prevention means for preventing exposure of the needlepoint.

This ensures that the needlepoint of the needle tube can be assuredly prevented from being exposed unintentionally, and the drug solution can be securely prevented from being accidentally caused to flow out through the needle tube.

In addition, in the drug solution injector according to the present invention, preferably, the operation mechanism is composed of a cover member supported by the support member so as to be displaceable to a first position for covering the needle tube up to the needlepoint, and to a second position for exposing the needlepoint through movement from the first position toward the proximal end, and the support member is preferably rotated when the cover member is in the first position.

This ensures that the needlepoint of the needle tube can be assuredly prevented from being exposed inadvertently, and the drug solution can be securely prevented from being accidentally caused to flow out through the needle tube.

Further, in the drug solution injector according to the present invention, preferably, the support member supports the cover member so that the cover member is rotatable around an axis of the outer cylinder and that the cover member is movable along the axial direction of the outer cylinder, and the proximal end of the flow channel is closed by a bottom portion of the outer cylinder to attain the blocked state when the cover member is in the first position, turning of the cover member in the first position around the axis of the outer cylinder releases the restraint on the cover member by the exposure prevention means and causes the proximal end of the flow channel to face the inside of the outer cylinder to attain the communicating state, and movement of the cover member from the first position to the second position in this communicating state causes the needlepoint to protrude from the cover member.

This ensures that the needlepoint of the needle tube can be assuredly prevented from being exposed inadvertently, and the drug solution can be securely prevented from being accidentally caused to flow out through the needle tube.

In addition, in the drug solution injector according to the present invention, preferably, the exposure prevention means restrains the cover member from moving from the first position to the second position.

Thus, the needlepoint of the needle tube can be securely prevented from being inadvertently caused to protrude from the cover member.

Further, in the drug solution injector according to the present invention, preferably, the cover member has a hollow cylindrical shape and has a tongue piece protruding in the proximal direction, and the exposure prevention means is composed of a projected part projectedly formed on an outer peripheral portion of the outer cylinder, and restrains movement of the cover member in the proximal direction through abutment of a proximal portion of the tongue piece on a distal portion of the projected part.

This ensures that the cover member cannot be displaced to the second position unless an operation of releasing the restraint on the movement of the cover member from the first position to the second position is performed. Therefore, even if an unintentional force along the proximal direction is exerted on the cover member, the needlepoint of the needle tube can be assuredly prevented from being inadvertently caused to protrude from the cover member. Consequently, a finger or the like can be securely prevented from being punctured by mistake by the needlepoint inadvertently protruded.

In addition, in the drug solution injector according to the present invention, preferably, the support member and the cover member each have hollow cylindrical portions, and constitute a fitting structure in which an outer peripheral portion of the cover member is fitted to an inner peripheral portion of the support member, and one of the outer peripheral portion of the support member and the inner peripheral portion of the cover member is formed with elongated ridges along the axial direction of the outer cylinder, whereas the other is inserted by the elongated ridges and formed with grooves for guiding the elongated ridges.

This ensures that when the cover member is moved between the first position and the second position, the elongated ridges are respectively guided by (slid within) the grooves, so that the operation of moving the cover member can be carried out smoothly.

Further, in the drug solution injector according to the present invention, preferably, the operation mechanism is composed of at least one of two members including: a cover member that is supported by the support member so as to be displaceable to a first position for covering the needle tube up to the needlepoint, and to a second position for exposing the needlepoint through movement from the first position in the proximal direction; and a cap which is detachably mounted on the outer cylinder, is connected so as to be capable of rotating the support member in the mounted state, and covers the needle tube up to the needlepoint.

This ensures that the needlepoint of the needle tube can be assuredly prevented from being exposed inadvertently, and the drug solution can be securely prevented from accidentally flowing out through the needle tube.

In addition, in the drug solution injector according to the present invention, preferably, the operation mechanism is composed of: a cover member that is supported by the support member so as to be displaceable to a first position for covering the needle tube up to the needlepoint and to a second position for exposing the needlepoint through movement from the first position in the proximal direction; and a cap which is detachably mounted on the outer cylinder, is connected so as to be capable of rotating the support member in the mounted state, and accommodates the cover member entirely therein.

This ensures that the needlepoint of the needle tube can be assuredly prevented from being exposed inadvertently, and the drug solution can be securely prevented from accidentally flowing out through the needle tube.

Further, in the drug solution injector according to the present invention, the support member supports the cap so that the cap can be turned around the axis of the outer cylinder and supports the cap so that the cap can be moved along the axial direction of the outer cylinder, and the proximal end of the flow channel is closed by a bottom portion of the outer cylinder in the blocked state, and turning of the cap around the axis of the outer cylinder from the blocked state causes the proximal end of the flow channel to face the inside of the outer cylinder to attain the communicating state, in which the cap can be disengaged through movement in the distal direction.

This ensures that the needlepoint of the needle tube can be assuredly prevented from being exposed inadvertently, and the drug solution can be securely prevented from accidentally flowing out through the needle tube.

In addition, in the drug solution injector according to the present invention, preferably, the cap has a hollow cylindrical portion, and constitutes a fitting structure wherein an outer peripheral portion of the outer cylinder is fitted in an inner peripheral portion of the cylindrical portion, and one of the inner peripheral portion of the cap and the outer peripheral portion of the outer cylinder is provided at least with a cam groove formed along the axial direction thereof, whereas the other is provided with a projected part which is engaged with and guided by the cam groove.

This ensures that the projected part is engaged with the cam groove in the mounted state. With the projected part guided by the cam groove, the cap is restrained from being turned around the axis, and can only be moved along the axial direction (in the distal direction).

Further, in the drug solution injector according to the present invention, preferably, in the mounted state, the cap constitutes a part of the exposure prevention means.

This ensures that in the mounted state, unintentional exertion of a pushing force on the cover member can be securely prevented, so that the cover member can be assuredly prevented from unintentionally moving from the first position to the second position, exposing the needlepoint.

In addition, in the drug solution injector according to the present invention, preferably, an operation of moving the cover member can be performed in a disengaged state wherein the cap has been disengaged.

This enables the drug solution injector to be used.

Further, in the drug solution injector according to the present invention, preferably, the support member and the cap each have hollow cylindrical portions, and constitute a fitting structure wherein an outer peripheral portion of the support member is fitted in an inner peripheral portion of the cap, and one of the inner peripheral portion of the cap and the outer peripheral portion of the support member is formed with an elongated (spline-like) ridge along the axial direction of the outer cylinder, whereas the other is formed with a groove in which the elongated ridge is inserted.

This ensures that with the cap rotated, the rotating force is transmitted to the support member through the groove and the elongated ridge, whereby the support member is rotated. Consequently, the communicating state and the blocked state can be selected assuredly.

In addition, in the drug solution injector, preferably, the operation mechanism has a biasing member for biasing the cover member in the distal direction.

This ensures that when the pushing force for pushing the cover member in the proximal direction is released, the cover member is assuredly moved in the distal direction, to be located in the first position. Accordingly, inadvertent exposure of the needlepoint can be prevented more securely.

Further, in the drug solution injector according to the present invention, preferably, the cap has a contact part with which the cover member biased in the distal direction by a biasing force of the biasing member makes contact.

This enables an operation of disengaging the cap to be carried out easily.

In addition, in the drug solution injector according to the present invention, preferably, the cap is biased in the distal direction by a biasing force of the biasing member through the cover member in the mounted state, and the biasing force assists disengagement of the cap when the cap is disengaged.

This enables an operation of disengaging the cap to be carried out easily.

Further, in the drug solution injector according to the present invention, preferably, the cover member has a bottomed hollow cylindrical shape, and a through-hole through which the needle tube can be passed is formed in a bottom portion of the cover member.

This ensures that when the cover member is displaced to the second position, the needlepoint of the needle tube protrudes in the distal direction from the cover member through the through-hole. In this state, a target part can be punctured by the needlepoint of the needle tube.

In addition, in the drug solution injector according to the present invention, preferably, when the cover member is moved from the second position to the first position, the needle tube is again covered up to the needlepoint by the cover member disposed in the first position.

This prevents mispuncture by the needlepoint.

Further, the drug solution injector according to the present invention, preferably, includes reprotrusion prevention means for preventing the needlepoint once protruded and retracted in relation to the cover member from again protruding from the cover member.

This enables the needlepoint of the needle tube once protruded and retracted in relation to the cover member to be securely prevented from again protruding from the cover member.

In addition, in the drug solution injector according to the present invention, preferably, the reprotrusion preventing means includes an inhibiting member which is disengageably mounted to the support member and which is clamped between the support member and the cover member when disengaged from the support member so as to inhibit the cover member from again moving to the second position, a biasing member for biasing the inhibiting member in the distal direction, and a lock part which is provided on the cover member and which locks the inhibiting member against a biasing force of the biasing member, and the inhibiting member is released from the locking by the lock part, to be disengageable from the support member by the biasing force of the biasing member, when the cover member moves from the first position to the second position.

This ensures that the needlepoint of the needle tube once protruded and retracted in relation to the cover member can be securely prevented, by a simple configuration, from again protruding from the cover member.

Further, in the drug solution injector according to the present invention, preferably, the cover member has a part functioning as a grip part which is gripped when the support member is operated.

This enables the support member to be operated easily.

In addition, in the drug solution injector according to the present invention, preferably, in the mounted state, an operation of moving the cover member cannot be carried out.

This ensures that in the mounted state, unintentional exertion of a pushing force on the cover member can be securely prevented from occurring. Accordingly, the cover member can be assuredly prevented from inadvertently moving from the first position to the second position, exposing the needlepoint.

Further, in the drug solution injector according to the present invention, preferably, the cap has a part functioning as a grip part which is gripped when the support member is operated.

This enables the support member to be operated easily.

In addition, in the drug solution injector according to the present invention, preferably, the support member has a cylindrical part having a hollow cylindrical shape, and constitutes a fitting structure wherein an outer peripheral portion of the outer cylinder is fitted in an inner peripheral portion of the cylindrical part.

This ensures the inner peripheral portion of the cylindrical part and the outer peripheral portion of the outer cylinder can slide relative to each other, so that the support member can be assuredly turned about the axis of the outer cylinder.

Further, in the drug solution injector according to the present invention, preferably, when the above-mentioned restraint is released, each of the projected parts is located between both tongue pieces, edge portions of both tongue pieces make contact with edge portions of each projected part, and turning of the cover member about the axis of the outer cylinder is restrained.

This ensures that the communication between the inside of the outer cylinder and the inside of the needle tube through the flow channel can be prevented from being again blocked due to closing of the proximal end of the flow channel by the bottom portion of the outer cylinder.

In addition, in the drug solution injector according to the present invention, preferably, when the cover member is moved from the first position to the second position, the edge portions of both tongue pieces slide on the edge portions of each projected part, whereby turning of the cover member about the axis of the outer cylinder is restrained.

This ensures that when the cover member is moving to the second position, the cover member is restrained (prevented) from rotating unintentionally. Therefore, the communication between the inside of the outer cylinder and the inside of the needle tube through the flow channel can be prevented from being again blocked due to closing of the proximal end of the flow channel by the bottom portion of the outer cylinder.

Further, in the drug solution injector according to the present invention, preferably, when the cover member is disposed in the first position, the locking force exerted on the inhibiting member by the lock part is in excess of the biasing force of the biasing member, and, when the cover member moves from the first position to the second position, the biasing force exceeds the locking force.

Thus, the locking of the inhibiting member is released, making the inhibiting member movable.

In addition, the drug solution injector according to the present invention, preferably, has a plunger which is connected to a proximal portion of the gasket and is operable to move the gasket in the axial direction of the outer cylinder.

This ensures that the gasket is moved in the distal direction by operating the plunger, whereby the drug solution is assuredly administered (injected) into a target part by sequentially passing through the flow channel in the support member and the lumen of the needle tube.

Further, in the drug solution injector according to the present invention, preferably, when the inside of the outer cylinder and the inside of the needle tube communicate with each other through the flow channel, movement of the gasket by operating the plunger is possible, and the movement of the gasket in the distal direction injects the drug solution into a target part through the needle tube.

This enables safe administration of the drug solution.

BEST MODE FOR CARRYING OUT THE INVENTION

A drug solution injector according to the present invention will be described in detail below, based on preferred embodiments shown in the accompanying drawings.

First Embodiment

Figure 6:
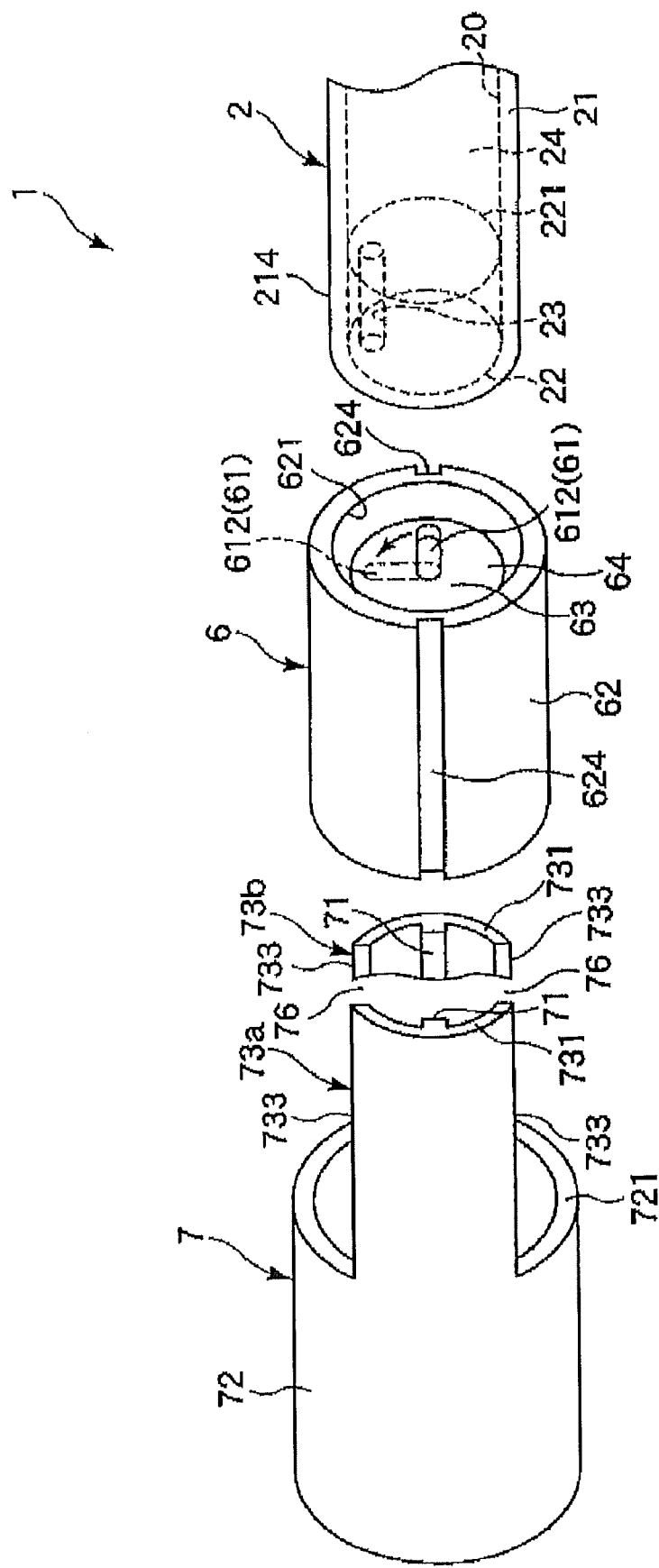
FIG. 6 is an exploded perspective view of the drug solution injector shown in FIG. 1.
Figure 7:
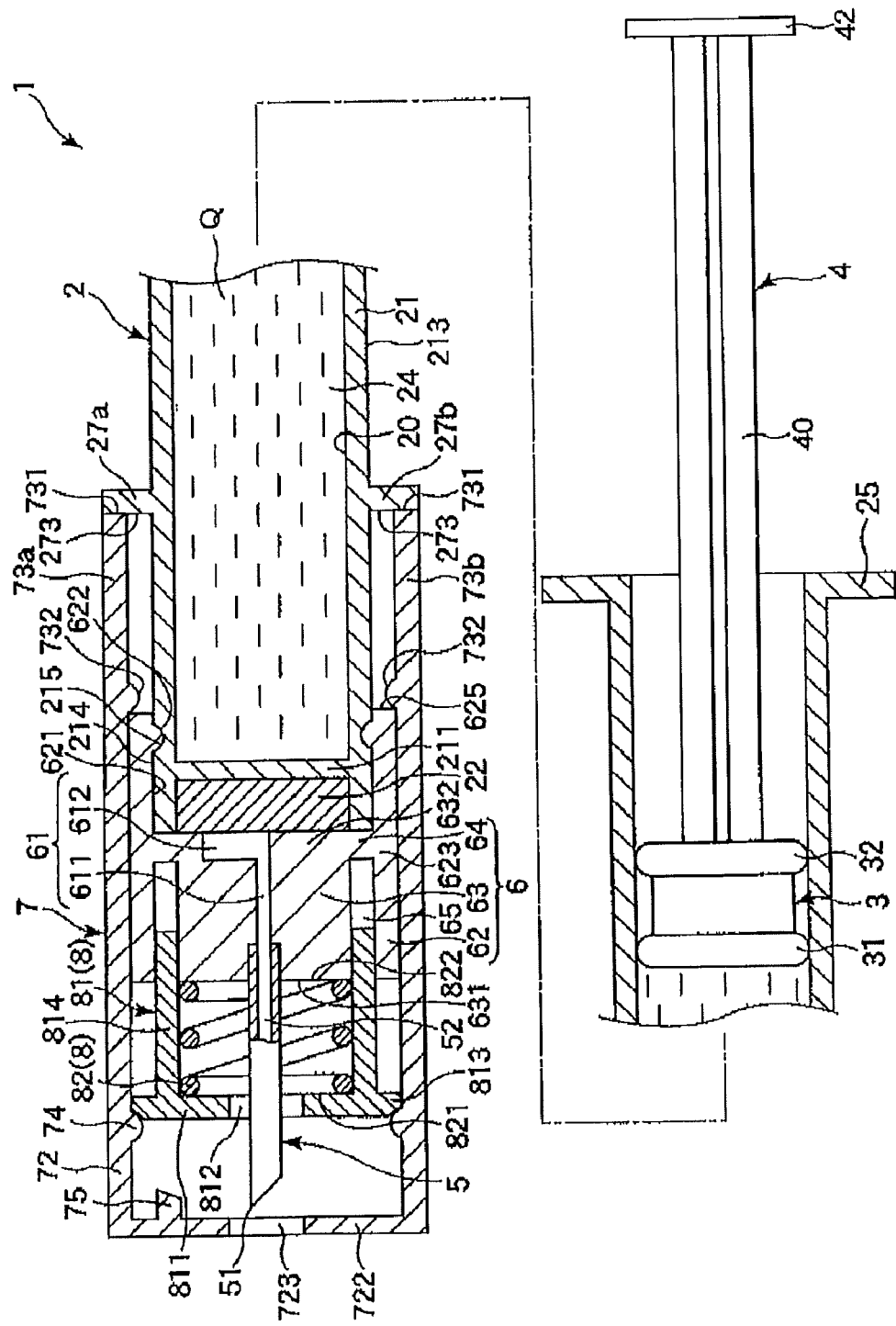
FIG. 7 is a longitudinal sectional view of the drug solution injector shown in FIG. 1.
Figure 8:
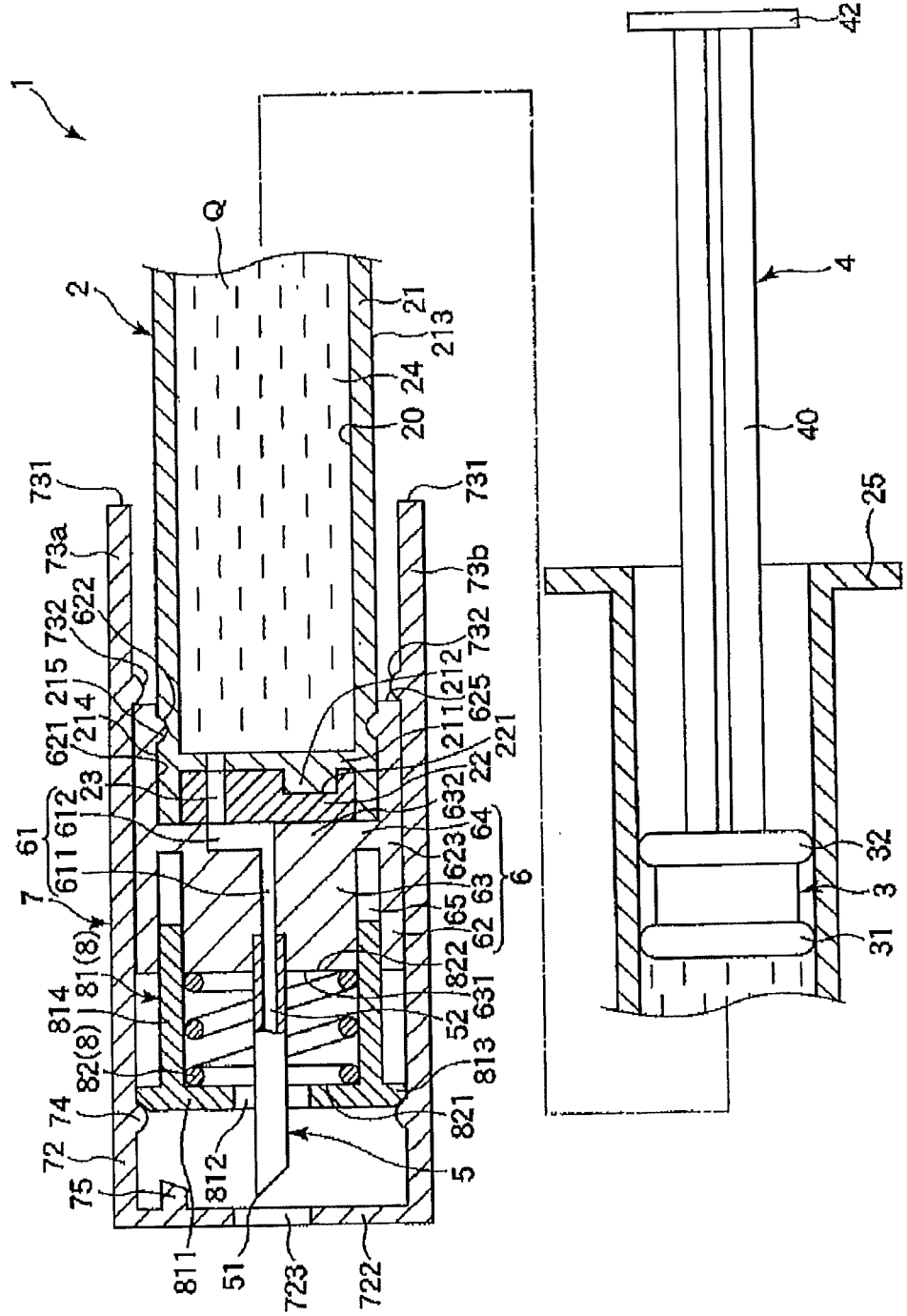
FIG. 8 is a longitudinal sectional view of the drug solution injector shown in FIG. 2.
Figure 9:
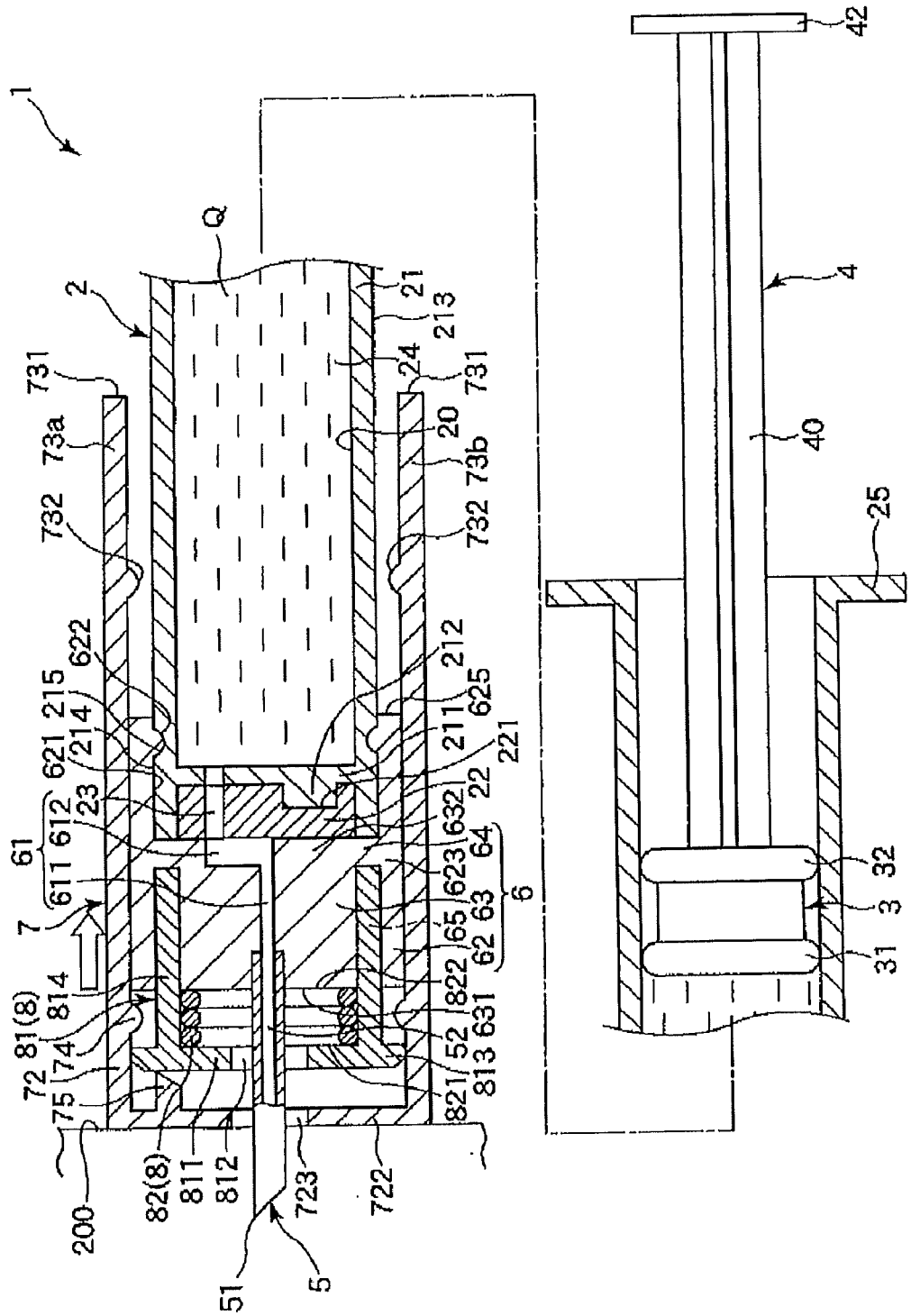
FIG. 9 is a longitudinal sectional view of the drug solution injector shown in FIG. 3.
Figure 10:
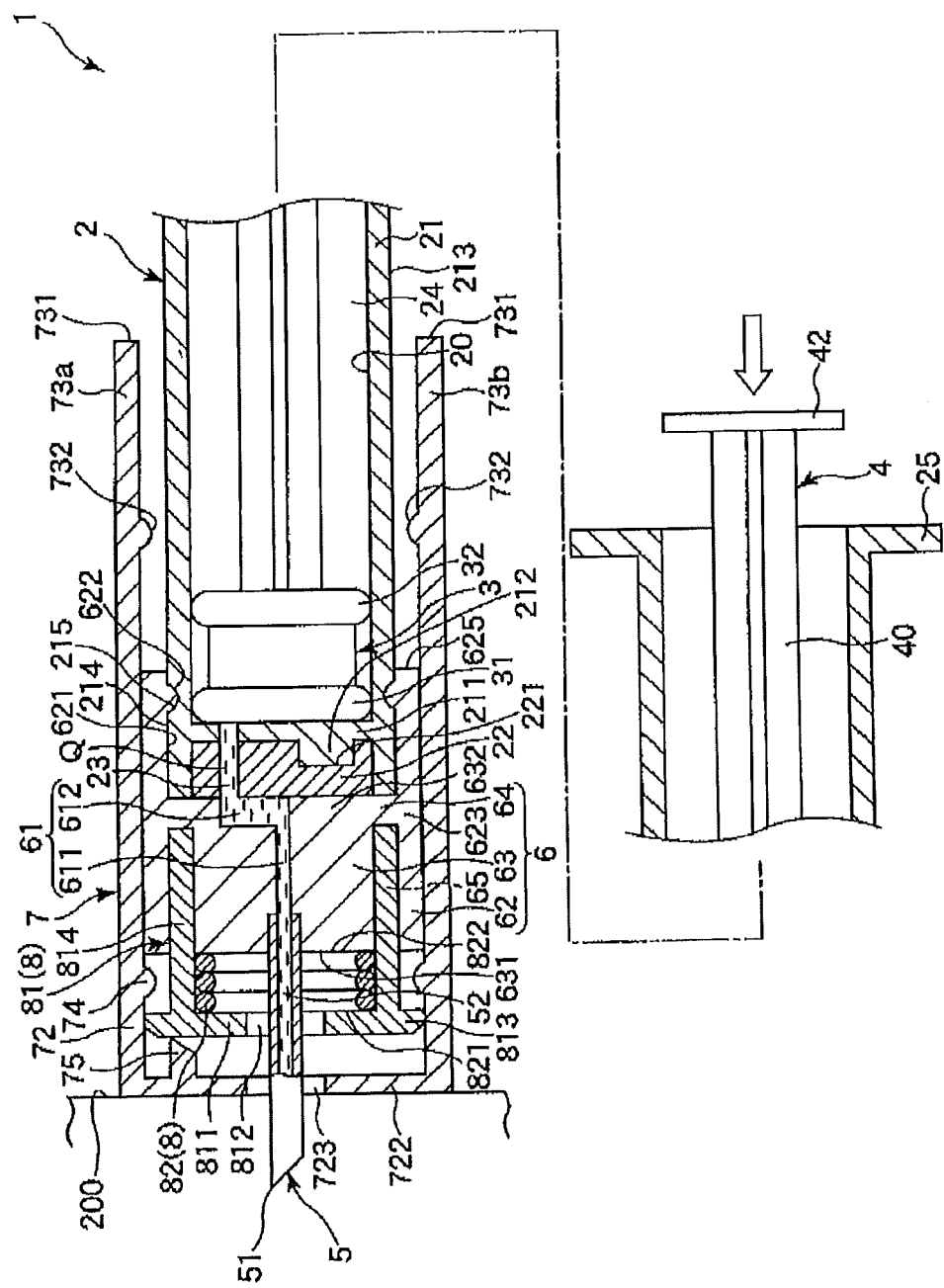
FIG. 10 is a longitudinal sectional view of the drug solution injector shown in FIG. 4.
Figure 11:
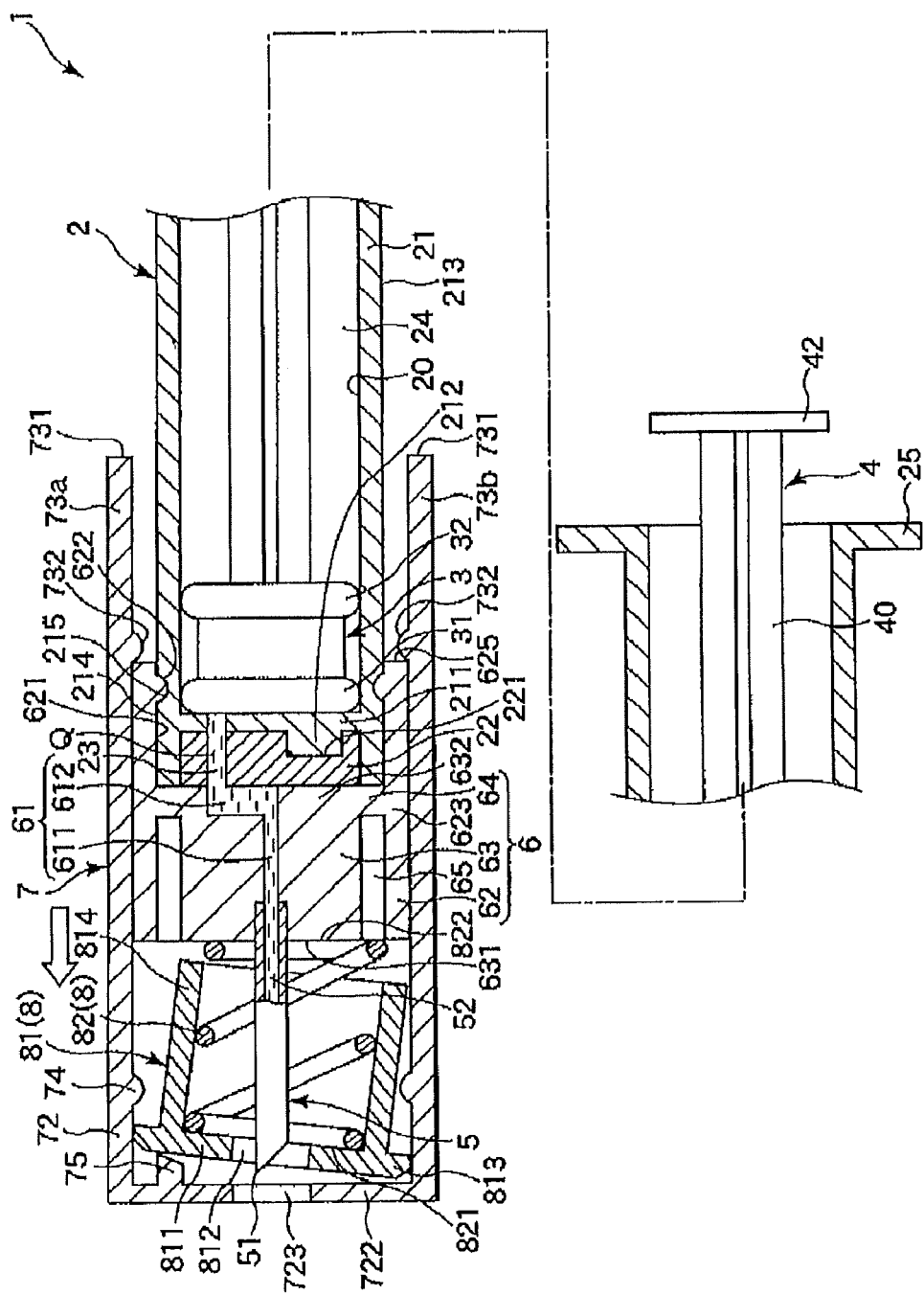
FIG. 11 is a longitudinal sectional view of the drug solution injector shown in FIG. 5.

FIGS. 1 to 5 are perspective views for sequentially illustrating the states in use of a drug solution injector (first embodiment) of the present invention; FIG. 6 is an exploded perspective view of the drug solution injector shown in FIG. 1; FIG. 7 is a longitudinal sectional view of the drug solution injector shown in FIG. 1; FIG. 8 is a longitudinal sectional view of the drug solution injector shown in FIG. 2; FIG. 9 is a longitudinal sectional view of the drug solution injector shown in FIG. 3; FIG. 10 is a longitudinal sectional view of the drug solution injector shown in FIG. 4; and FIG. 11 is a longitudinal sectional view of the drug solution injector shown in FIG. 5. Incidentally, in the following, for convenience of description, the right upper side in FIGS. 1 to 5 will be referred to as "proximal", and the left lower side as "distal", the right side in FIGS. 6 to 11 will be referred to as "proximal", and the left side as "distal".

The drug solution injector 1 shown in the respective drawings is a syringe preliminarily filled with a drug solution Q, to be used in injecting (administering) the drug solution Q into a living body. The drug solution injector 1 includes an outer cylinder (syringe outer cylinder) 2 having a bottomed hollow cylindrical shape, a gasket 3 slidable in the outer cylinder 2, a plunger 4 connected to a proximal portion of the gasket 3, a needle tube 5 located on the distal side of the outer cylinder 2, a support member (connecting member) 6 for interconnecting the outer cylinder 2 and the needle tube 5, a cover member 7 supported on the outer peripheral side of the outer cylinder 2 with the support member 6 interposed therebetween, and an inhibiting member 81 and a coil spring (biasing member (inhibiting member biasing member)) 82 which collectively serve as reprotrusion prevention means 8 for preventing reprotrusion of a needlepoint 51 of the needle tube 5. The configuration of each of these parts will be described below.

Incidentally, the drug solution Q preliminarily filled in the drug solution injector 1 is appropriately selected according to the purpose of use thereof. Examples of the drug solution Q include those drug solutions which are injected mainly by hypodermic injection, such as hematinic, vaccine, hormone products, antirheumatic, carcinostatic, anesthetic, and anticoagulant.

As shown in FIGS. 7 to 11, the outer cylinder 2 is composed of a bottomed hollow cylindrical member having a bottom portion 211.

The outer cylinder 2 is formed integrally with a plate-like flange 25 at the proximal outer periphery thereof. At the time of moving the plunger 4 relative to the outer cylinder 2 and in other similar situations, the operation can be performed with a finger or fingers put on the flange 25.

A packing (sealing member) 22 composed of an elastic material is secured to a distal-side portion of the bottom portion 211 of the outer cylinder 2. The packing 22 has a circular disc-like shape, and is fixed to the outer cylinder 2 by fitting.

In addition, a recess 221 is formed in a proximal portion of the packing 22 at an eccentric position relative to the center thereof (see, for example, FIG. 8). A projected part 212 formed on the bottom portion 211 of the outer cylinder 2 at a portion corresponding to the recess 221 is inserted in the recess 221. With the projected part 212 inserted in the recess 221, the packing 22 is fixed to the outer cylinder 2 more securely, so that relative turning of the packing 22 and the outer cylinder 2 can be prevented from occurring.

As shown in FIG. 8 (and also in FIGS. 9 to 11), the outer cylinder 2 has a flow channel 23 which extends through both the bottom portion 211 and the packing 22. The flow channel 23 communicates with a lumen (space 24) inside the outer cylinder 2. This enables the drug solution Q in the space 24 to pass through the flow channel 23.

As shown in FIG. 7 (and also in FIGS. 1 to 5), a body part (outer cylinder main body 21) of the outer cylinder 2 has a pair of projected parts (movement restraint means (exposure prevention means)) 27a and 27b formed at distal-side portions of an outer peripheral portion 213 thereof. These projected parts 27a and 27b restrain the cover member 7 from being inadvertently moved. With the cover member 7 restrained from being moved in the proximal direction, inadvertent exposure of the needlepoint 51 from the cover member 7 can be prevented from occurring. Further, these projected parts 27a and 27b are disposed so as to face each other with the axis of the outer cylinder 2 interposed therebetween.

Since the projected parts 27a and 27b are substantially the same in configuration, the projected part 27a will be described below as a representative of both of them.

Figure 1:
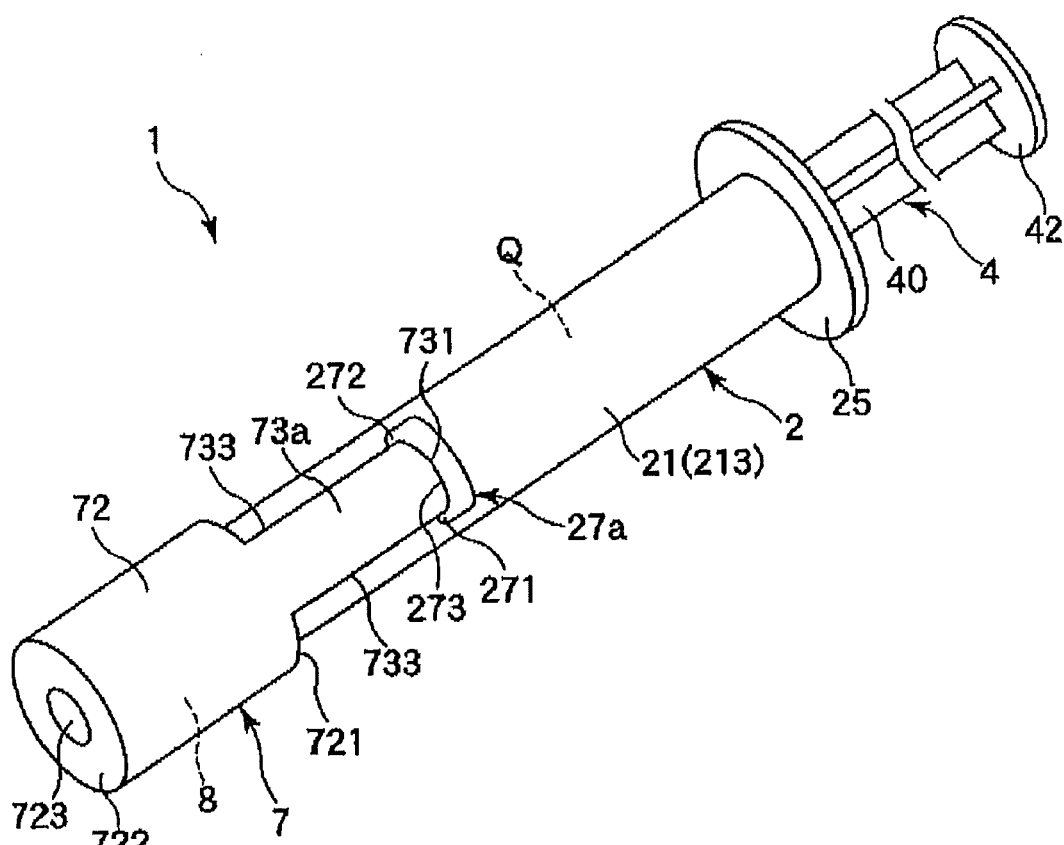
FIG. 1 is a perspective view for sequentially illustrating the states in use of a drug solution injector (first embodiment) of the present invention.

As shown in FIG. 1, the projected part 27a is elongated along the circumferential direction of the outer cylinder 2. Claw parts 271 and 272 are integrally formed at edge portions of the projected part 27a, namely, at both end portions of the projected part 27a in the longitudinal direction. The claw parts 271 and 272 are formed to project in the distal direction.

Examples of materials for forming the outer cylinder 2 and the plunger 4 to be described later include various resins such as cyclic polyolefins, polyvinyl chloride, polyethylene, polypropylene, polystyrene, poly-(4-methylpentene-1), polycarbonate, acrylic resins, acrylonitrile-butadiene-styrene copolymer, polyesters such as polyethylene terephthalate, etc., butadiene-styrene copolymer, polyamides, polyethersulfones, polysulfones, etc., among which preferred are such resins as cyclic polyolefins, polypropylene, polyesters, poly-(4-methylpentene-1), polyether-sulfones, and polysulfones, because they are easy to mold. Incidentally, the material constituting the outer cylinder 2, preferably, is substantially transparent for securing visibility of the inside.

In addition, the outer cylinder 2 is preferably provided with graduations (not shown) on the outer peripheral portion 213 (outer peripheral surface) thereof. This makes it possible to check the amount of the drug solution Q contained in the drug solution injector 1.

The gasket 3 composed of an elastic material is accommodated in the outer cylinder 2 as above. The gasket 3 is provided, at its outer peripheral portion, with two annular projected parts 31 and 32 at a predetermined interval along the axial direction. The projected parts 31 and 32 are kept in close contact with the inner peripheral surface 20 of the outer cylinder 2 and are slidable, whereby air-tightness (liquid-tightness) can be securely maintained and enhanced slidability can be obtained. Also, the space 24 surrounded by the gasket 3 and the outer cylinder 2 can be filled with the drug solution Q.

Examples of materials for forming the gasket 3 and the packing 22 include various rubber materials (especially vulcanized ones) such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluororubber, etc., various thermoplastic elastomers based on styrene, polyolefin, polyvinyl chloride, polyurethane, polyester, polyamide, polybutadiene, transpolyisoprene, fluororubber, chlorinated polyethylene or the like, and comparatively flexible resin materials such as polyethylene, polyvinyl chloride resin, etc., which may be used either singly or in mixture of two or more of them.

The plunger 4 is connected to a proximal portion of the gasket 3. The plunger 4 is operable for moving the gasket 3 in the inside of the outer cylinder 2 along the axial direction. Incidentally, the method for connecting the plunger 4 to the gasket 3 is not particularly limited, and examples of the method include screw engagement, fitting, etc.

The plunger 4 has a main body part 40 composed mainly of plate pieces which are arranged in the shape of a cross in traverse section, and, at the proximal end thereof, a flange-like (plate-like) finger holding part 42 is formed integrally with the main body part 40. When the finger holding part 42 is pushed by a finger or the like, the plunger 4 is moved in the distal direction.

On the distal side of the outer cylinder 2, the needle tube 5 which is hollow is disposed along the axial direction of the outer cylinder 2. The needle tube 5 is secured to the support member 6, and a lumen 52 of the needle tube 5 communicates with a junction flow channel (flow channel) 61 formed in the support member 6. In addition, according to the position of the junction flow channel 61 (support member 6), the lumen 52 of the needle tube 5 is made to communicate with the space 24 (flow channel 23) inside the outer cylinder 2 through the junction flow channel 61 (the junction flow channel 61 indicated by two-dotted chain line in FIG. 6; see FIGS. 8 to 10) or the communication is blocked (the junction flow channel 61 indicated by solid line in FIG. 6; see FIG. 7).

At the distal end of the needle tube 5, the sharp needlepoint 51 is formed. The shape of the needlepoint 51 is not particularly limited. In this embodiment, the needlepoint 51 has a cutting edge surface inclined at a predetermined angle to the axis of the needle tube 5.

The needle tube 5 is made of a metallic material, such as stainless steel, aluminum or aluminum alloy, titanium or titanium alloy, or the like.

Examples of the method for firmly attaching (securing) the needle tube 5 to the support member 6 include fitting, caulking, fusing, adhesion with an adhesive, etc., or various combinations thereof.

As shown in FIGS. 7 and 8, the needle tube 5 is connected to the outer cylinder 2 through the support member 6. The support member 6 has a cylindrical part 62 having a hollow cylindrical shape, a columnar part 63 having a solid cylindrical shape and disposed inside the cylindrical part 62, and a link part 64 interlinking the cylindrical part 62 and the columnar part 63.

The inside diameter of the cylindrical part 62 is set to be approximately as large as the outer shape of the outer cylinder 2. This enables a distal outer peripheral portion 214 of the outer cylinder 2 (outer cylinder main body 21) to be fitted in a proximal inner peripheral portion 621 of the cylindrical part 62. As a result, the support member 6 has a fitting structure formed by the cylindrical part 62. This fitting structure enables relative sliding of the proximal inner peripheral portion 621 of the cylindrical part 62 and the distal outer peripheral portion 214 of the outer cylinder 2, and, therefore, the support member 6 (cylindrical part 62) can be turned about the axis of the outer cylinder 2 reliably.

Further, the cylindrical part 62 is provided, at its proximal inner peripheral portion 621, with an annular projected part 622 formed in the circumferential direction thereof. The projected part 622 is inserted in a recess 215 formed circumferentially in the distal outer peripheral portion 214 of the outer cylinder 2. This securely prevents the support member 6 from being inadvertently disengaged from the outer cylinder 2.

As shown in FIG. 6, the cylindrical part 62 is provided, in its outer peripheral portion, with a pair of guide grooves (grooves) 624 along its longitudinal direction. These guide grooves 624 are arranged so as to face each other with the axis of the cylindrical part 62 interposed therebetween. In each of the guide grooves 624, each of elongated ridges 71 of the cover member 7 to be described later is inserted.

The columnar part 63 is disposed inside the cylindrical part 62, with a gap 65 therebetween. The columnar part 63 has an overall length (height) set to be shorter than the overall length of the cylindrical part 62. The columnar part 63 is located on the distal side in the cylindrical part 62, and a proximal portion 632 of the columnar part 63 is connected to a portion near a central portion 623 of the cylindrical part 62 through the link part 64.

In addition, the above-mentioned needle tube 5 is fixed to the center of a distal portion of the columnar part 63. The columnar part 63 is formed therein with the junction flow channel 61 communicating with the lumen 52 of the needle tube 5. The junction flow channel 61 extends through the columnar part 63, and is formed into the shape of letter "L" in longitudinal sectional view (side view) (see FIG. 7). Therefore, the junction flow channel 61 is divided into a first flow channel 611 formed along the axial direction of the columnar part 63, and a second flow channel 612 formed in a direction orthogonal to the first flow channel 611.

The distal end of the first flow channel 611 is connected to the proximal end of the needle tube 5, and the junction flow channel 61 communicates with the lumen 52 of the needle tube 5 through the distal end of the first flow channel 611.

As shown in FIG. 6, the second flow channel 612 is composed of an elongated recess opening in a proximal end face of the columnar part 63. According to the position around the axis of the support member 6, the second flow channel 612 can assume a state of being closed with the packing 22 of the outer cylinder 2 (a state shown in FIG. 7) and a state of being opened toward the flow channel 23 in the outer cylinder 2 and communicating with the flow channel 23 (a state shown in FIGS. 8 to 11). In the configuration shown in FIG. 6, when the support member 6 is rotated counterclockwise by 90°, the second flow channel 612 is displaced from the state of being closed by the packing 22 of the outer cylinder 2 to the state of communicating with the flow channel 23.

Incidentally, the material for forming the support member 6 is not particularly limited, and, for example, the same materials as those mentioned as to the outer cylinder 2 above can be used.

By the support member 6 as above, the cover member 7 is supported. The cover member 7 can cover (surround) the needle tube 5. The cover member 7 can be displaced to a first position (see FIGS. 1, 2, 5, 7, 8 and 11) for covering the needle tube 5 up to the needlepoint 51 and displaced from the first position along the axial direction of the outer cylinder 2 to a second position (see FIGS. 3, 4, 9 and 10) for exposing the needlepoint 51.

As shown in FIG. 1, the cover member 7 has a main body part 72 having a bottomed hollow cylindrical shape, and a pair of tongue pieces 73a and 73b projectingly formed at a proximal end 721 of the main body part 72. The tongue piece 73a and the tongue piece 73b are disposed so as to face each other with the axis of the main body part 72 (outer cylinder 2) interposed therebetween.

The inside diameter of the main body part 72 is set to be substantially as large as the outer shape of the cylindrical part 62 of the support member 6. Thus, the main body part 72 is fitted in the cylindrical part 62 reliably.

In addition, at the inner peripheral portion of the cover member 7, a pair of elongated ridges 71 are formed along the axial direction of the main body part 72 (outer cylinder 2) over the range from the main body part 72 to the tongue pieces 73a and 73b. Of the two elongated ridges 71, one elongated ridge 71 is disposed on the side of the tongue piece 73a, while the other ridge 71 is disposed on the side of the tongue piece 73b.

In other words, the two elongated ridges 71 are disposed so as to face each other with the axis of the cover member 7 interposed therebetween.

Each of the elongated ridges 71 is inserted in each guide groove 624 in the support member 6. Thus, when the cover member 7 is moved between the first position and the second position, each of the elongated ridges 71 is guided by (slid along) the guide groove 624, so that the cover member 7 can be moved smoothly (see FIG. 3). In addition, by the just-mentioned insertion, relative rotation of the cover member 7 and the support member 6 is restrained (inhibited). Consequently, when the cover member 7 is rotated about the axis of the outer cylinder 2, the cover member 7 is rotated together with the support member 6 relative to the outer cylinder 2, and, therefore, the rotating operation can be carried out smoothly (see FIG. 2).

The main body part 72 has a through-hole 723 formed in a central portion of a bottom portion (distal wall part) 722 thereof, and the needle tube 5 can be inserted (passed) through the through-hole 723. When the cover member 7 is displaced to the second position, the needlepoint 51 of the needle tube 5 can protrude in the distal direction from the cover member 7 through the through-hole 723. In this state, a living body surface (target part) 200 can be punctured with the needlepoint 51 of the needle tube 5 (see FIGS. 9 and 10).

The main body part 72 is provided, at its proximal end 721, with the pair of tongue pieces 73a and 73b projecting in the proximal direction. Each of the tongue pieces 73a and 73b is a long body having an arcuate cross-sectional shape along the circumferential direction of the cylindrical part 62 of the support member 6.

In addition, on the inner peripheral portion of the tongue pieces 73a and 73b, engaging parts 732 for engagement with a proximal end 625 of the cylindrical part 62 of the support member 6 are projectingly formed. By engagement of the engaging parts 732 with the proximal end 625 of the cylindrical part 62 of the support member 6, the cover member 7 can be prevented from being disengaged from the support member 6 in the distal direction.

As shown in FIGS. 1 and 7, when the drug solution injector 1 is in an initial state (unused state), the cover member 7 is located in the first position. In this instance, a proximal portion 731 of the tongue piece 73a is in abutment on a distal portion 273 of the projected part 27a of the outer cylinder 2, and a proximal portion 731 of the tongue piece 73b is in abutment on a distal portion 273 of the projected part 27b of the outer cylinder 2. This restrains the movement of the cover member 7 in the proximal direction, specifically, the movement from the first position to the second position (hereinafter, this restraint will be referred to as "restraint on movement"). Unless an operation of releasing this restraint on movement is performed, the cover member 7 cannot be displaced to the second position. Therefore, even if an inadvertent external force in the proximal direction is exerted on the cover member 7, inadvertent protrusion of the needlepoint 51 of the needle tube 5 from the cover member 7 is securely prevented from occurring. Accordingly, mispuncture of a finger of the like by the needlepoint 51 being inadvertently caused to protrude can be securely prevented from occurring.

Further, as shown in FIG. 1, the tongue piece 73a in abutment on the projected part 27a of the outer cylinder 2 is clamped between the claw part 271 and the claw part 272 of the projected part 27a. The same applies also to the tongue piece 73b in abutment on the projected part 27b of the outer cylinder 2. By such clamping, inadvertent rotation of the cover member 7 is restrained, and, therefore, the restraint on movement of the cover member 7 by the projected parts 27a and 27b can be prevented from being released inadvertently. Thus, the cover member 7 is prevented from being inadvertently moved from the first position to the second position, so that inadvertent protrusion of the needlepoint 51 of the needle tube 5 from the cover member 7 is securely prevented from occurring.

Incidentally, as shown in FIG. 7, in the initial state of the drug solution injector 1, the junction flow channel 61 (second flow channel 612) in the support member 6 is sealed with the packing 22 of the outer cylinder 2, and, therefore, the communication between the space 24 inside the outer cylinder 2 and the lumen of the needle tube 5 through the junction flow channel 61 is blocked.

Figure 2:
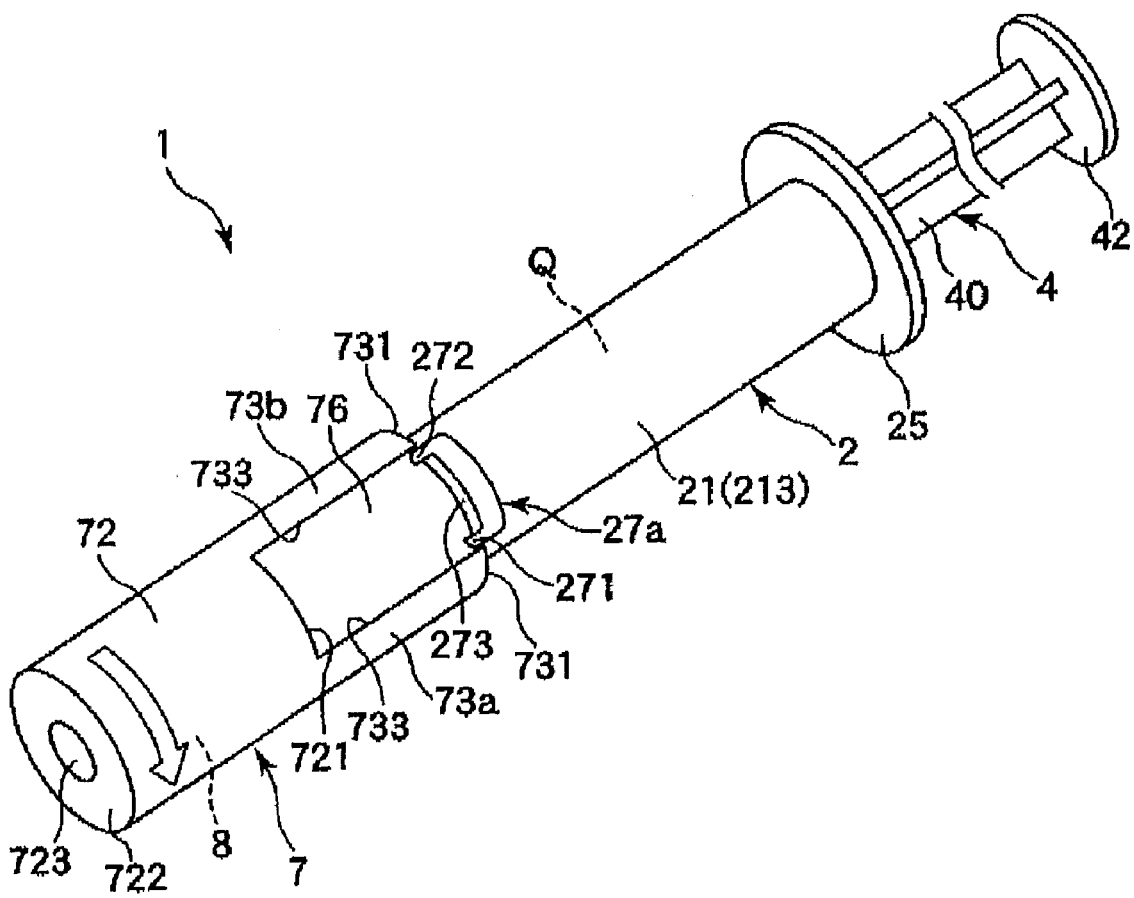
FIG. 2 is a perspective view for sequentially illustrating the states in use of the drug solution injector of the present invention.

When the cover member 7 is rotated from the state shown in FIG. 1 in the direction of arrow in FIG. 2, the tongue piece 73a rides over the claw part 271 of the projected part 27a of the outer cylinder 2, and the projected part 27a enters (is located) into a cutout 76 formed between the tongue piece 73a and the tongue piece 73b; similarly, the projected part 27b also enters into a cutout 76 on the side opposite to the above-mentioned cutout 76. This releases the restraint on movement (see FIGS. 2 and 8). In the drug solution injector 1, the operation of rotating the cover member 7 from the condition shown in FIG. 1 in the direction of the arrow in FIG. 2 may be referred to as "restraint-on-movement releasing operation."

With the restraint on movement thus released, it becomes possible to move the cover member 7 in the proximal direction. Therefore, the cover member 7 can be moved from the first position to the second position (see FIG. 3).

Incidentally, as shown in FIG. 8, when the cover member 7 is rotated, the junction flow channel 61 (second flow channel 612) in the support member 6 is displaced to a position corresponding to the flow channel 23 in the outer cylinder 2. Consequently, the space 24 inside the outer cylinder 2 and the lumen 52 of the needle tube 5 communicate with each other through the junction flow channel 61.

In addition, as shown in FIG. 2, when the restraint on movement is released, the projected part 27a (and the projected part 27b, as well) is located between the tongue piece 73a and the tongue piece 73b. In this instance, a side portion (edge portion) 733 of the tongue piece 73a makes contact with the claw part 271 (edge portion) of the projected part 27a, and a side portion 733 of the tongue piece 73b makes contact with a claw part 272 (edge portion). This restrains (prevents) the cover member 7 from being rotated (turned) further, so that the junction flow channel 61 in the support member 6 can be prevented from parting from the flow channel 23 in the outer cylinder 2 to be sealed again with the packing 22 of the outer cylinder 2.

Figure 3:
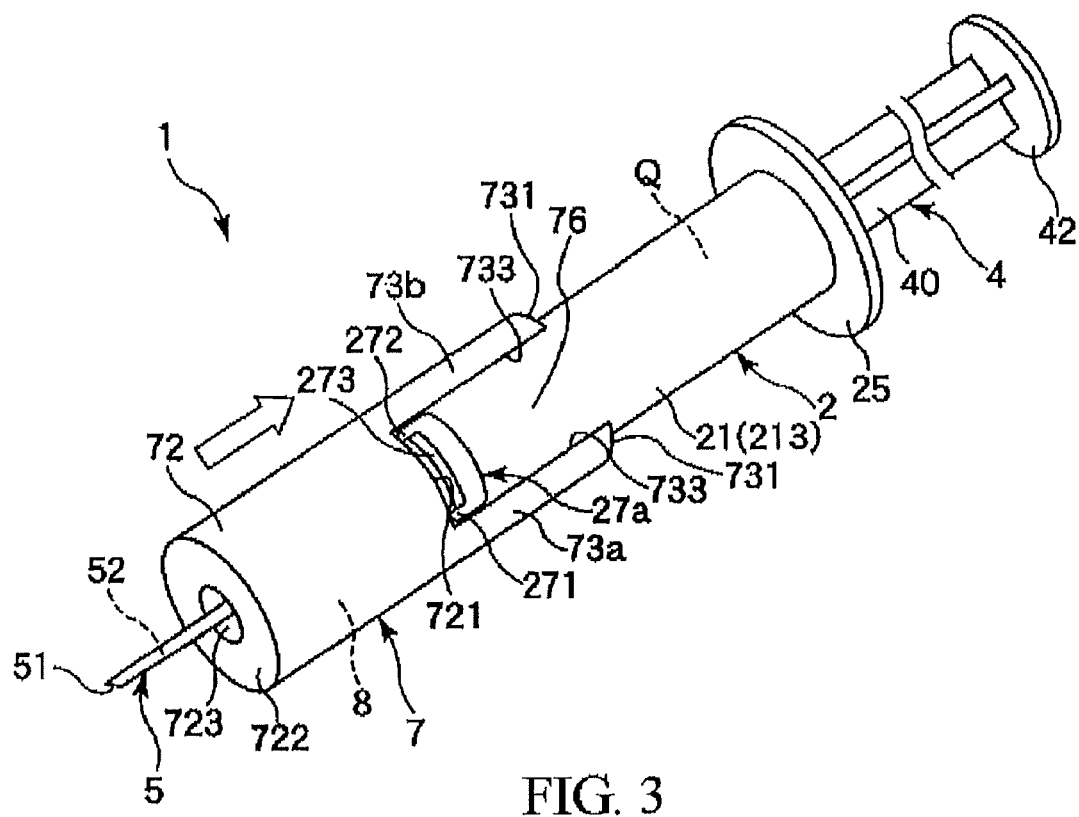
FIG. 3 is a perspective view for sequentially illustrating the states in use of the drug solution injector of the present invention.

When the cover member 7 is moved from the state shown in FIG. 2 in the direction of the arrow in FIG. 3, the side portion 733 of the tongue piece 73a slides on the claw part 271 of the projected part 27a (and the projected part 27b, as well), and the side portion 733 of the tongue piece 73b slides on the claw part 272 of the projected part 27a (and the projected part 27b, as well). Thus, the cover member 7 is restrained (prevented) from being turned inadvertently while the cover member 7 is being moved in the proximal direction. Therefore, as above-mentioned, the junction flow channel 61 in the support member 6 can be prevented from parting from the flow channel 23 in the outer cylinder 2 to be sealed again with the packing 22 of the outer cylinder 2.

Figure 4:
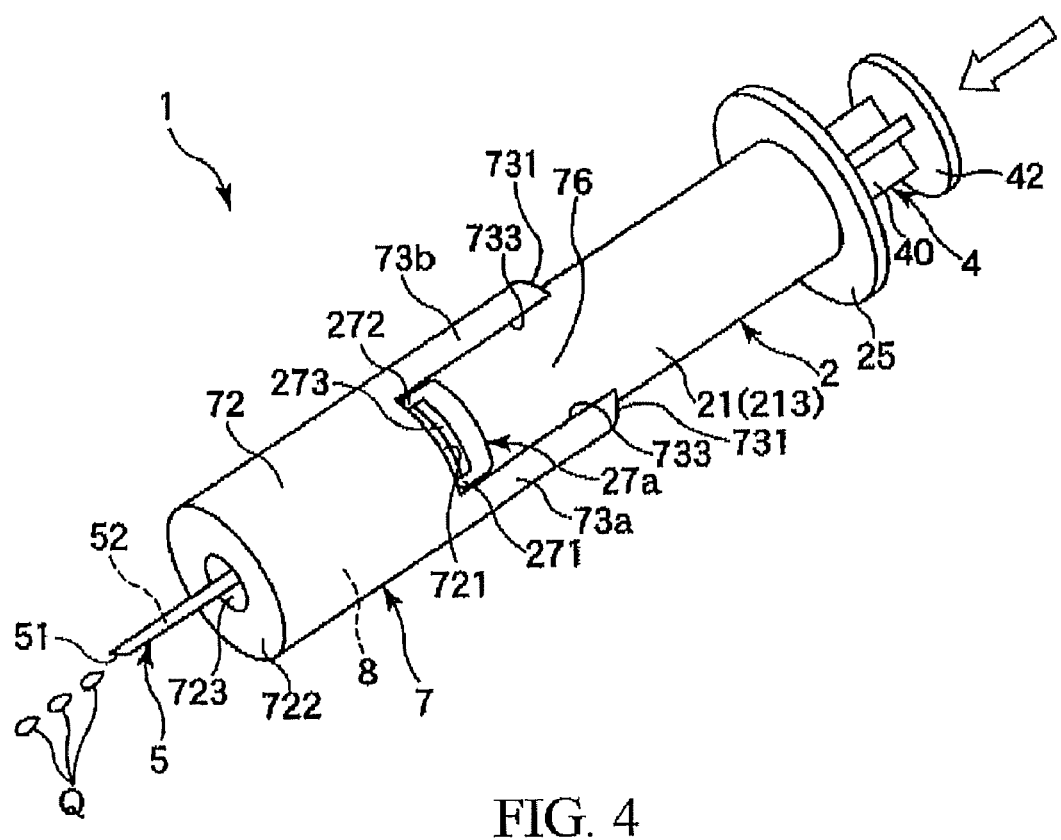
FIG. 4 is a perspective view for sequentially illustrating the states in use of the drug solution injector of the present invention.

As shown in FIGS. 3 and 4, when the cover member 7 is moved to the second position, the needlepoint 51 of the needle tube 5 protrudes from the through-hole 723 in the cover member 7.

Figure 5:
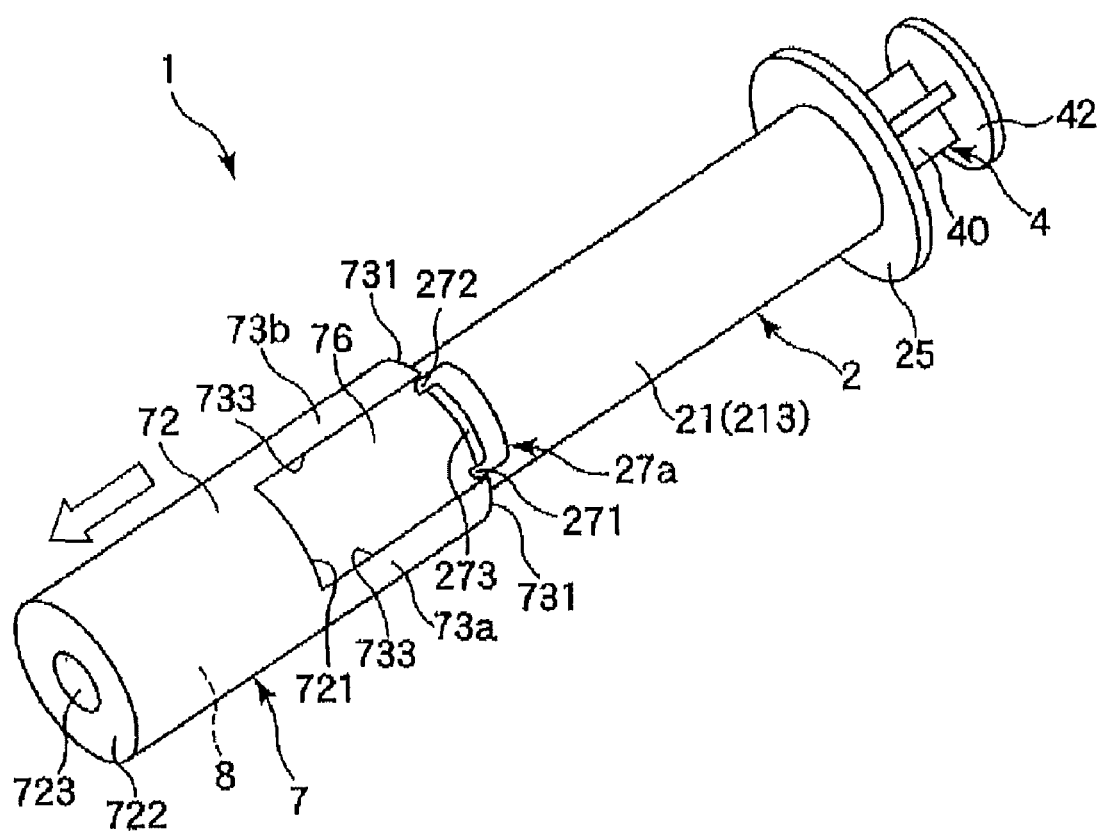
FIG. 5 is a perspective view for sequentially illustrating the states in use of the drug solution injector of the present invention.

In addition, in the drug solution injector 1, the cover member 7 can be moved again from the second position to the first position by moving the cover member 7 from the condition shown in FIG. 4 in the direction of the arrow in FIG. 5. By the cover member 7 thus returned to the first position, the needle tube 5 can be covered again up to the needlepoint 51.

Incidentally, the material for forming the cover member 7 is not particularly limited. For example, the same materials as those mentioned as to the outer cylinder 2 above can be used. In addition, the material forming the cover member 7, preferably, is substantially transparent for securing visibility. Thus, when the cover member 7 is pressed against a puncture site on a living body surface 200 as shown in FIG. 9, the pressing operation can be carried out while checking the puncture site through the cover member 7. Consequently, the puncture site can be punctured with the needlepoint 51 reliably.

Next, the reprotrusion prevention means 8 will be described below.

As mentioned above, the needle tube 5 can be protruded and retracted with respect to the cover member 7. The reprotrusion prevention means 8 prevents the needle tube 5 (needlepoint 51) that has been protruded and thereafter retracted with respect to the cover member 7 from being protruded again from the cover member 7. The reprotrusion prevention means 8 has the inhibiting member 81 detachably mounted to the support member 6, and a coil spring 82 for biasing the inhibiting member 81 in the distal direction.

The inhibiting member 81 has a bottomed hollow cylindrical shape. A bottom portion (distal wall part) 811 of the inhibiting member 81 is provided, in its central portion, with a through-hole 812 through which the needle tube 5 passes. In addition, a flange 813 enlarged in diameter in its outer shape is formed along the outer periphery of the bottom portion 811.

As shown in FIG. 7, in the initial state of the drug solution injector 1, the inhibiting member 81 has a part (proximal portion) of a side wall 814 inserted into the gap 65 in the support member 6. In addition, the coil spring 82 is accommodated in the inhibiting member 81 in the state of having a distal end 821 of the coil spring 82 in abutment on the bottom portion 811 of the inhibiting member 81 and having its proximal end 822 thereof in abutment on a distal end face 631 of the columnar part 63 of the support member, while being in a compressed state. Thus, the inhibiting member 81 is biased in the distal direction by a biasing force of the coil spring 82.

Further, in this condition, the flange 813 is in contact with (is locked by) a lock part 74 protruding from an inner peripheral portion of the cover member 7 (main body part 72). The lock part 74 is formed in an annular form along the inner circumference of the cover member 7. By such a lock part 74, the inhibiting member 81 is locked with respect to the cover member 7, against the biasing force of the coil spring 82. Therefore, when the cover member 7 is in the first position, a locking force exerted on the inhibiting member 81 by the lock part 74 is in excess of the biasing force of the coil spring 82.

When the cover member 7 is rotated relative to the outer cylinder 2 from the state shown in FIG. 7, the restraint on movement is released (see FIG. 8).

When the cover member 7 is moved to the second position, as shown in FIG. 9, the lock part 74 presses the inhibiting member 81 in the proximal direction against the biasing force of the coil spring 82. This causes the side wall 814 of the inhibiting member 81 to slide in the gap 65. This movement of the inhibiting member 81 compresses the coil spring 82 further, and, eventually, the biasing force of the coil spring 82 comes to exceed the locking force exerted by the lock part 74. As a result, the flange 813 rides over the lock part 74, and the flange 813 is released from the locking state. In this instance, the inhibiting member 81 is pressed by the biasing force of the coil spring 82 for moving in the distal direction, but its movement in the distal direction is restrained because the inhibiting member 81 is brought into abutment on a projection 75 formed integrally and projectingly at the bottom portion 722 of the cover member 7.

In addition, as mentioned above, when the cover member 7 is moved to the second position, the needlepoint 51 of the needle tube 5 protrudes through the through-hole 723 in the cover member 7. Also, in this condition, the plunger 4 can be operated (see FIG. 10).

When an operating force (pushing force) for moving the cover member 7 to the second position is released, as shown in FIG. 11, the coil spring 82 restores its shape by its own elastic force (restoring force). Thus, the inhibiting member 81 is moved in the distal direction, and its side wall 814 comes out of, or is disengaged from, the gap 65 in the support member 6. In addition, the inhibiting member 81 presses the cover member 7 in the distal direction through the projection 75 of the cover member 7. As a result, the cover member 7 is returned to the first position, and the entire needle tube 5 is accommodated again into the cover member 7.

Also, the inhibiting member 81 disengaged from the support member 6 is sandwiched between the distal end face 631 of the support member 6 and the bottom portion 722 of the cover member 7 having returned to the first position. Further, the inhibiting member 81 is rotated clockwise in FIG. 11, with the projection 75 of the cover member 7 as the center of rotation, by the biasing force of the coil spring 82, and then, the axis of the inhibiting member 81 is inclined with respect to the axis of the cover member 7. Consequently, it becomes impossible for the side wall 814 of the inhibiting member 81 to be inserted again into the gap 65 in the support member 6 and slide within the gap 65.

When the cover member 7 is moved again in the proximal direction in the condition shown in FIG. 11, such a moving operation is prohibited (inhibited) by the inhibiting member 81.

Incidentally, the setting of the magnitude relationship between "the locking force exerted on the inhibiting member 81 by the lock part 74" and "the biasing force of the coil spring 82" can be performed, for example, by changing the angle of inclination of the lock part 74 relative to the inner peripheral portion of the cover member 7, or changing the spring constant of the coil spring 82.

In addition, in the drug solution injector 1, the lock part 74 and the projection 75 of the cover member 7 can be regarded as constituting part of the reprotrusion prevention means 8.

Further, the material for forming the inhibiting member 81 is not particularly limited, and, for example, the same materials as those mentioned as to the outer cylinder 2 above can be used. In addition, the material for forming the coil spring 82 is not particularly limited, and, for example, such metallic materials as stainless steel can be used.

Now, an example of the method for using the drug solution injector 1 will be described below.

[1] First, the drug solution injector 1 preliminarily filled with the drug solution Q in a sufficient amount for administration into a living body is prepared (see FIGS. 1 and 7). The drug solution injector 1 is an unused one, wherein the cover member 7 is in the first position. This ensures that the needle tube 5 is covered up to its needlepoint 51, so that mispuncture with the needlepoint 51 is securely prevented from occurring. In the drug solution injector 1, further, restraint on movement of the cover member 7 is offered by the projected parts 27a and 27b of the outer cylinder 2. This ensures that protrusion of the needlepoint 51 of the needle tube 5 from the through-hole 723 in the cover member 7 due to inadvertent movement of the cover member 7 in the proximal direction can be securely prevented from occurring. Therefore, mispuncture with the needlepoint 51 is prevented more assuredly.

Further, in the drug solution injector 1, as above-mentioned, the second flow channel 612 of the junction flow channel 61 is closed with the packing 22 of the outer cylinder 2. Therefore, communication between the space 24 inside the outer cylinder 2 and the lumen 52 of the needle tube 5 through the junction flow channel 61 is blocked. As a result, even if a force for pushing the plunger 4 is exerted inadvertently, inadvertent flow-out of the drug solution Q through the needle tube 5 is securely prevented, and, therefore, the drug liquid Q is prevented from being lost uselessly. In addition, since liquid-tightness of the space 24 inside the outer cylinder 2 is maintained, a sterilized state of the drug solution Q is maintained.

[2] Next, the cover member 7 is gripped and rotated in the direction of arrow in FIG. 2 starting from the state shown in FIG. 1, whereby the restraint on movement of the cover member 7 is released (see FIG. 2). In this instance, as above-mentioned, the flow channel 612 of the junction flow channel 61 is displaced to the position for opening toward the second flow channel 23 in the outer cylinder 2, so that the space 24 inside the outer cylinder 2 and the lumen 52 of the needle tube 5 communicate with each other through the junction flow channel 61. This communicating state is maintained until the drug solution Q is administered into the living body (see FIG. 8).

Thus, in the drug solution injector 1, the cover member 7 can be said to be an operation member (operation mechanism) for selection (change-over) between a communicating state wherein the space 24 inside the outer cylinder 2 and the lumen 52 of the needle tube 5 communicate with each other and a blocked state wherein the communication is blocked. In addition, the cover member 7 functions as a grip part such that an outer peripheral portion of the main body part 72 thereof is gripped at the time of operating the support member 6 (performing a change-over operation).

[3] Subsequently, while gripping the outer cylinder 2, the bottom portion 722 of the cover member 7 is pressed against the puncture part (target part) of a living body surface 200 against the biasing force of the coil spring 82 starting from the condition shown in FIG. 2 (and FIG. 8, as well), whereby the cover member 7 is moved into the second position (see FIG. 3). This results in that the needlepoint 51 of the needle tube 5 having been covered with the cover member 7 is protruded in the distal direction through the through-hole 723 in the cover member 7, to puncture the living body surface 200 (see FIG. 9).

[4] Next, starting from the condition shown in FIG. 3 (and FIG. 9, as well), an index finger and a middle finger having been gripping the outer cylinder 2 are put on an edge portion of the flange 25 of the outer cylinder 2, and a thumb is put on the finger holding part 42 of the plunger 4. Then, the finger holding part 42 is pushed in the distal direction by the thumb (see FIGS. 4 and 10). By this operation, the gasket 3 is moved in the distal direction, and therefore, the drug solution Q in the space 24 inside the outer cylinder 2 is reliably administered (injected) into the living body by sequentially passing through the flow channel 23 in the outer cylinder 2, the junction flow channel 61 in the support member 6, and the lumen 52 of the needle tube.

[5] After the administration of the drug solution Q, the drug solution injector 1 (cover member 7) is separated from the living body surface 200. In this instance, as above-mentioned, the cover member 7 is pushed in the distal direction through the inhibiting member 81 by the restoring force of the coil spring 82, to be returned into the first position (see FIGS. 5 and 11). As a result, the needle tube 5 is again covered up to its needlepoint 51. Therefore, scattering of blood in contact with the needlepoint 51 or mispuncture with the needlepoint 51 carrying the blood in contact therewith can be prevented from occurring, so that infection with the blood can be prevented from occurring.

Further, in the drug solution injector 1, as has been mentioned above, the inhibiting member 81 is separated from the support member 6 by the restoring force of the coil spring 82, and is located in an inclined posture between the distal end face 631 of the support member 6 and the bottom portion 722 of the cover member 7 (see FIG. 11). When it is attempted to again move the cover member 7 in the proximal direction in this condition, such a moving operation is prohibited by the inhibiting member 81. Consequently, erroneous use of a used drug solution injector 1, specifically, protruding the needle tube 5 of the used drug solution injector 1 and dosing the living body with the drug solution Q through the needle tube 5, can be securely prevented from occurring.

In addition, in this embodiment, of the support member 6 and the cover member 7, the support member 6 is formed with the guide grooves 624 whereas the cover member 7 is formed with the elongated ridges 71. However, this configuration is not limited, and a configuration may be adopted in which the cover member 7 is formed with guide grooves like the guide grooves 624 whereas the support member 6 is formed with elongated ridges like the elongated ridges 71.

Further, the tongue pieces 73a and 73b may be formed to project from the proximal end of the main body part 72 having a bottomed hollow cylindrical shape, or the main body part 72 may be provided with cutouts extending from the proximal end thereof and the remaining portions thereof are made to be the tongue pieces 73a and 73b.

Second Embodiment

Figure 12:
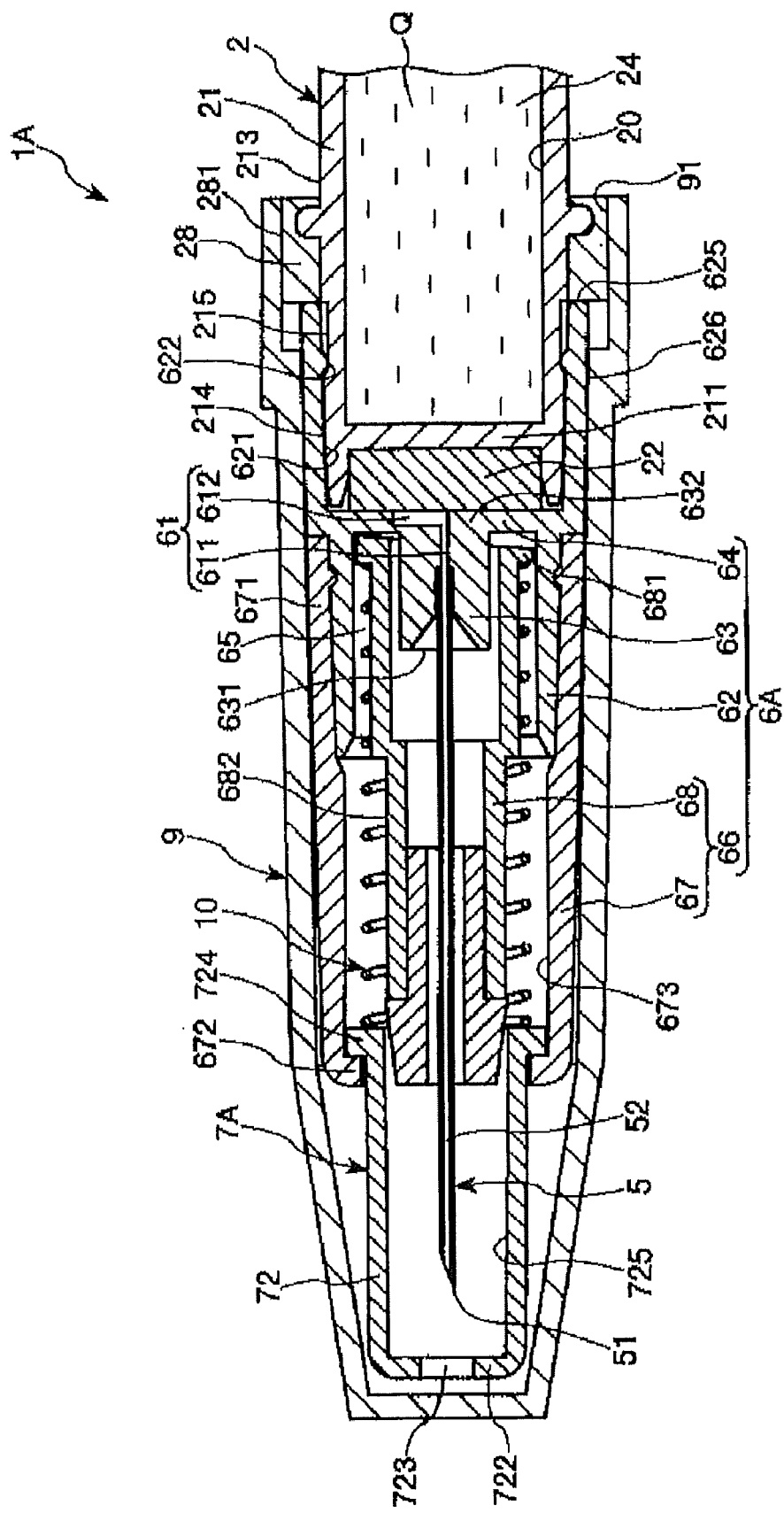
FIG. 12 is a longitudinal sectional view for sequentially illustrating the states in use of a drug solution injector (second embodiment) of the present invention.
Figure 18:
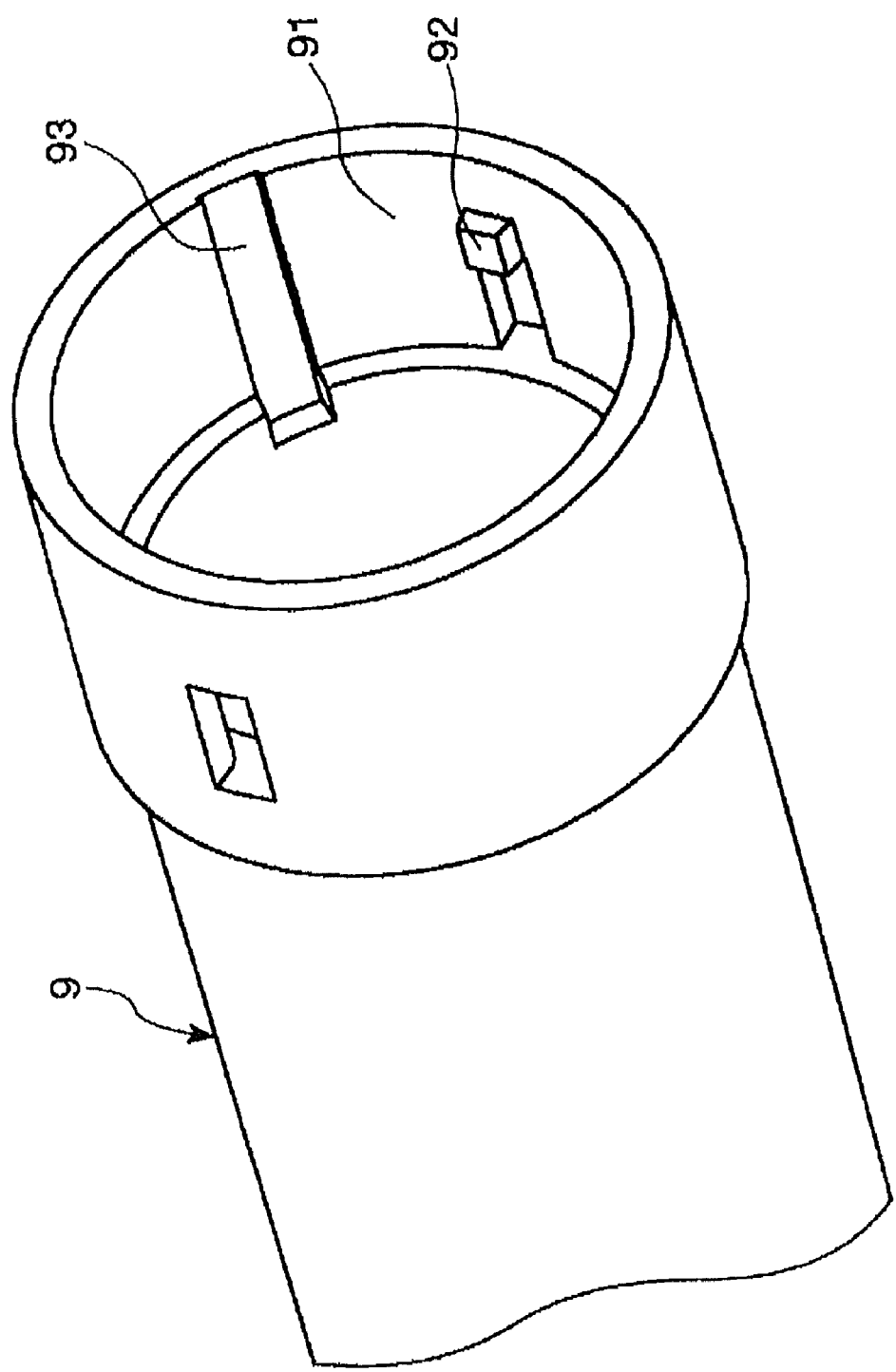
FIG. 18 is a perspective view of the vicinity of a proximal portion of a cap in the drug solution injector shown in FIG. 12 (and also in FIGS. 13 to 17)
Figure 19:
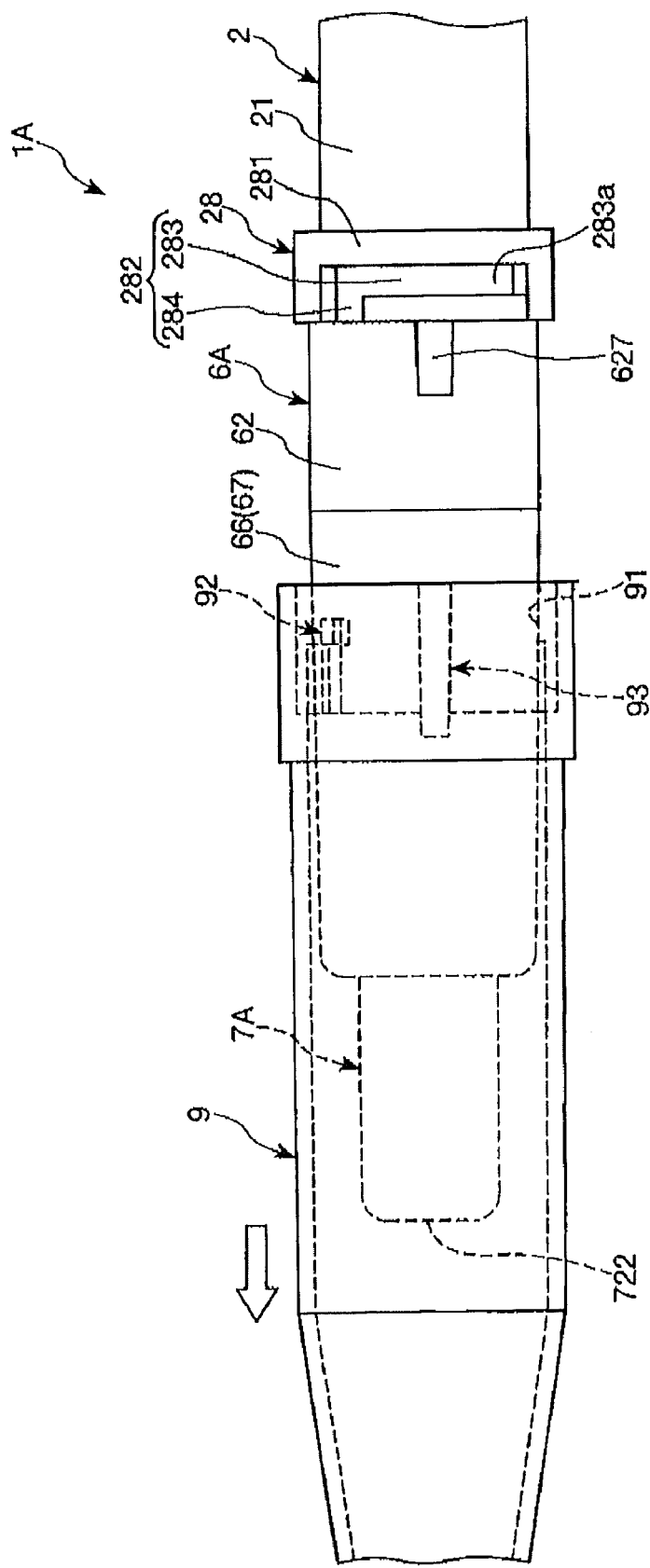
FIG. 19 is a plan view (a plan view corresponding to FIG. 14) showing a condition where the cap is disengaged in the drug solution injector according to the present invention.

FIGS. 12 to 17 are longitudinal sectional views for sequentially illustrating the states in use of a drug solution injector (second embodiment) of the present invention, FIG. 18 is a perspective view of the vicinity of a proximal portion of a cap in the drug solution injector shown in FIG. 12 (and FIGS. 13 to 17, as well), and FIG. 19 is a plan view (a plan view corresponding to FIG. 14) showing the condition where a cap in a drug solution injector of the present invention is disengaged. Incidentally, in the following, for convenience of description, the right side in FIGS. 12 to 19 will be referred to as "proximal", and the left side as "distal".

Now, a second embodiment of the drug solution injector according to the present invention will be described below referring to these drawings. The following description will be centered on differences from the above-described embodiment, and descriptions of the same items as above will be omitted.

This embodiment is the same as the first embodiment above, except for differences in the configuration in the operation mechanism.

In a drug solution injector 1A shown in FIGS. 12 to 17, an operation mechanism for rotating a support member 6A is composed of a cover member 7A, a coil spring (biasing member (cover member biasing member)) 10 for biasing the cover member 7A in the distal direction, and a cap 9 detachably mounted to an outer cylinder 2.

The support member 6A has an auxiliary part 66 for movably supporting the cover member 7A and the biasing member 10. The auxiliary part 66 is composed of a first member 67 which is fixed to a distal-side portion of a link part 64 of a cylindrical part 62, and a second member 68 inserted in a gap 65 between the cylindrical part 62 and a columnar part 63.

The first member 67 is composed of a hollow cylindrical body. The first member 67 has its proximal portion 671 fixed to the cylindrical part 62. The method for fixing here is not particularly limited, and examples of the fixing method include fitting, engagement, adhesion (adhesion with an adhesive or a solvent), and fusing (heat fusing, high-frequency fusing, ultrasonic fusing, etc.). In addition, in the vicinity of the distal end of the first member 67, a reduced-diameter part 672 reduced in inside diameter is formed. The inside diameter of the reduced-diameter part 672 is slightly greater than the outside diameter of a main body part 72 of the cover member 7A. This enables the main body part 72 of the cover member 7A to be inserted in and passed through the reduced-diameter part 672 (see FIGS. 12 to 18). Further, the reduced-diameter part 672 can abut on a flange part 724 of the cover member 7A to prevent the cover member 7A from being disengaged from the first member 67 (auxiliary part 66) (see, for example, FIG. 12).

The second member 68 is composed of a hollow cylindrical body. The second member 68 is provided at its proximal portion with a flange part 681 enlarged in outside diameter. The flange part 681 functions as a seat part (abutment part) on which the proximal end of the coil spring 10 is abutted (supported). In addition, the flange part 681 is biased in the proximal direction by a biasing force of the coil spring 10, to be abutted on the link part 64. In this embodiment, a distal end face of the first member 67 and a distal end face of the second member 68 are located at substantially the same position in the axial direction.

Materials for forming the first member 67 and the second member 68 are not particularly limited, and, for example, the same materials as those mentioned as to the support member 6 described in the first embodiment above can be used.

Figure 14:
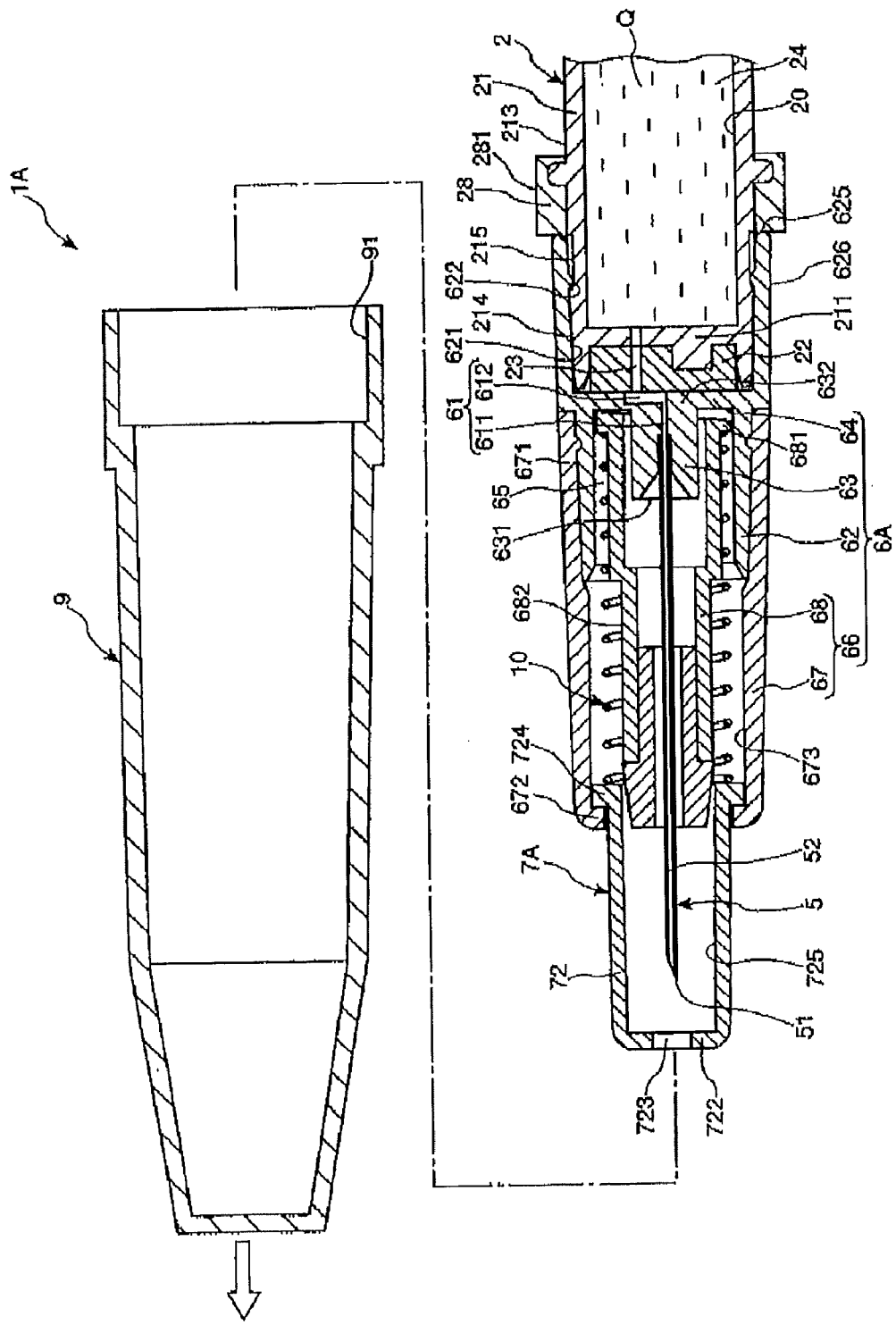
FIG. 14 is a longitudinal sectional view for sequentially illustrating the states in use of the drug solution injector (second embodiment) of the present invention.
Figure 15:
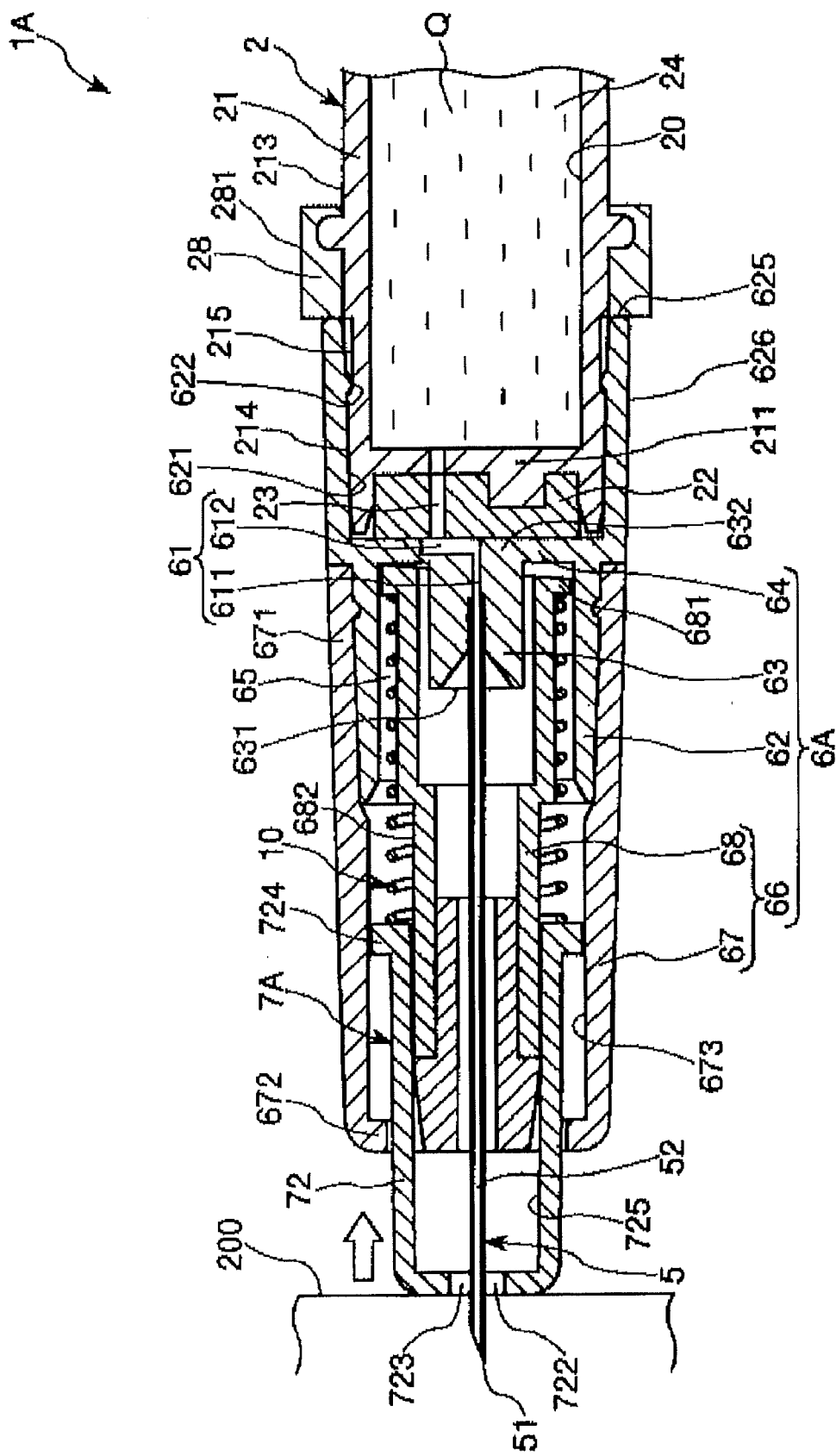
FIG. 15 is a longitudinal sectional view for sequentially illustrating the states in use of the drug solution injector (second embodiment) of the present invention.
Figure 16:
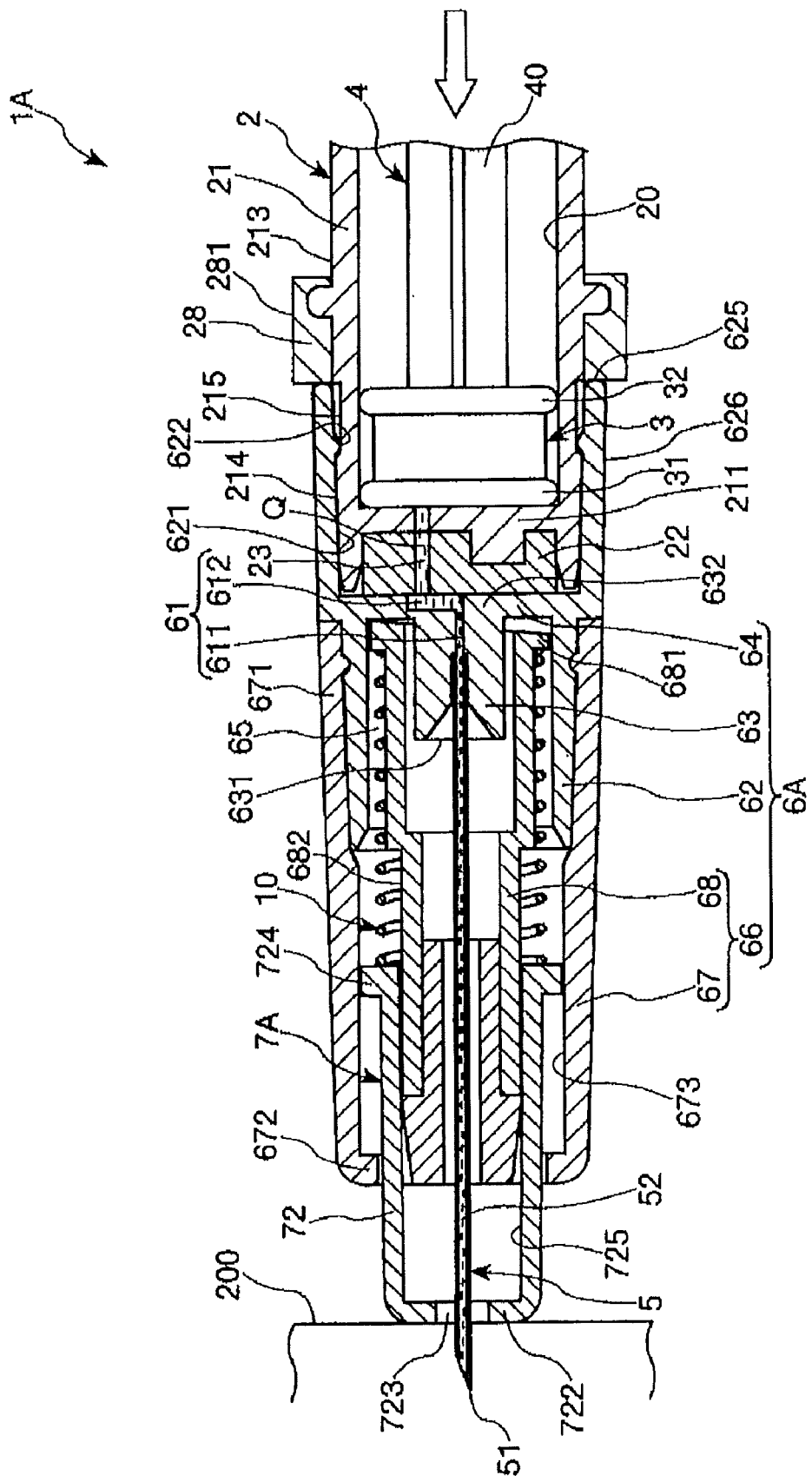
FIG. 16 is a longitudinal sectional view for sequentially illustrating the states in use of the drug solution injector (second embodiment) of the present invention.
Figure 17:
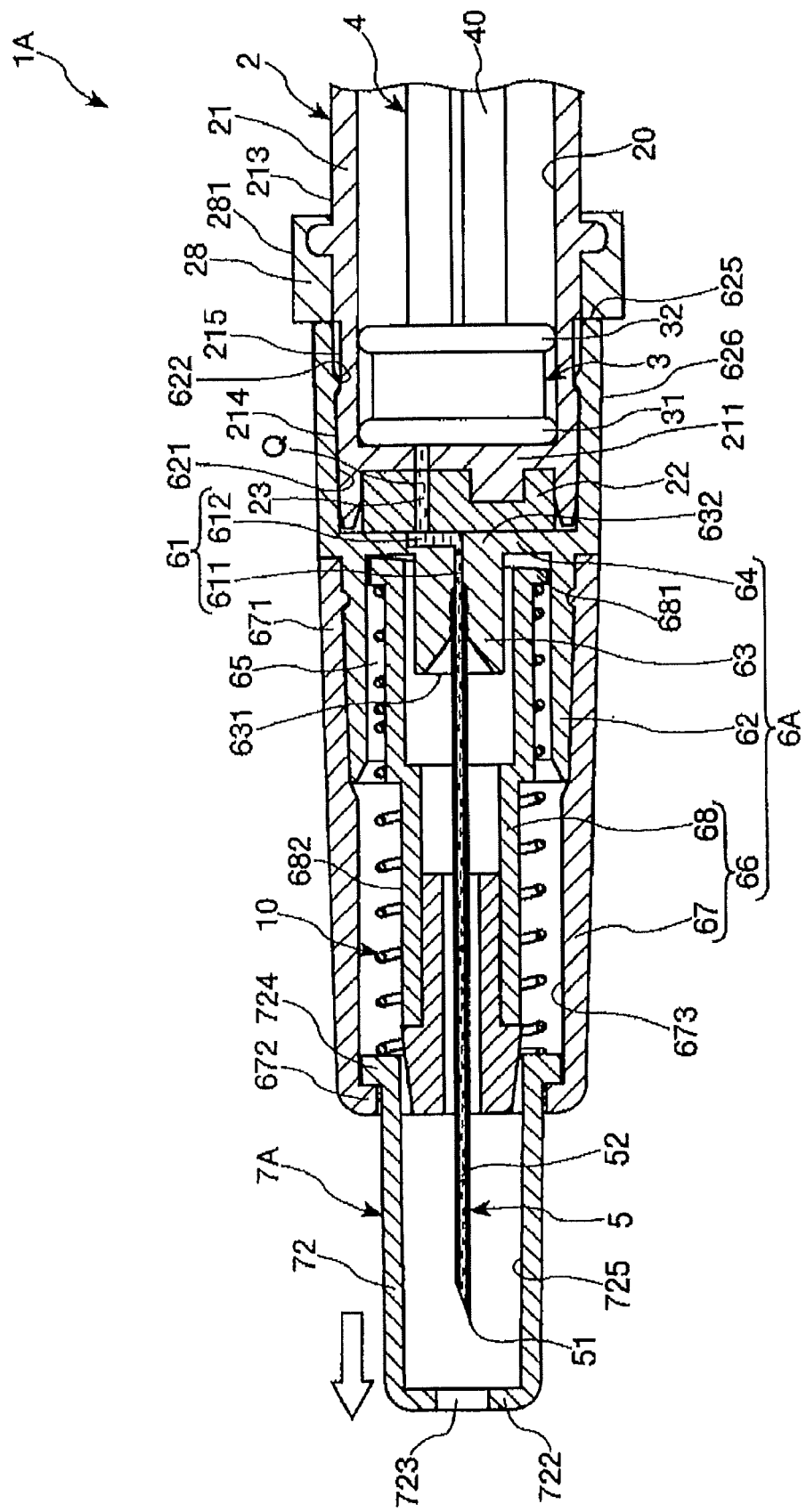
FIG. 17 is a longitudinal sectional view for sequentially illustrating the states in use of the drug solution injector (second embodiment) of the present invention.

The cover member 7A can be moved into a first position shown in FIG. 12 (and FIGS. 13, 14, and 17, as well) and a second position shown in FIG. 15 (and FIG. 16, as well). The cover member 7A is provided with the flange part 724 enlarged in outside diameter, at a proximal portion of the main body part 72 thereof. As above-mentioned, the flange part 724 abuts on the reduced-diameter part 672 of the first member 67 (auxiliary part 66) when the cover member 7A is in the first position.

In addition, when the cover member 7A is moved between the first position and the second position, the flange part 724 slides on an inner peripheral portion 673 of the first member 67 of the auxiliary part 66, and an inner peripheral portion 725 of the cover member 7A (main body part 72) slides on an outer peripheral portion 682 of the second member 68. This enables stable movement of the cover member 7A.

The coil spring 10 is disposed between the inner peripheral portion 673 of the first member 67 and an outer peripheral portion 682 of the second member 68. The coil spring 10 has its distal end in abutment on the flange part 724 of the cover member 7A, and has its proximal end in abutment on the flange part 681 of the second member 68. As shown in FIG. 15, when the cover member 7A being in the first position is pushed in the proximal direction in the condition where the cap 9 is disengaged (hereinafter, this condition will be referred to as "disengaged state"), the cover member 7A is moved in the proximal direction (to the second position) against the biasing force of the coil spring 10. When the pushing force on the cover member 7A is then released, the cover member 7A being in the second position is moved in the distal direction by the biasing force of the coil spring 10, to be returned into the first position again (see FIG. 17). Thus, in the disengaged state, puncture of a living body with the needlepoint 51 can be performed. In other words, the drug solution injector 1A can be used.

Incidentally, when the cover member 7A is in the first position, the coil spring 10 may be in the state of being compressed between the flange part 724 of the cover member 7A and the flange part 681 of the second member 68 (compressed state), or may be in a natural state (natural length) with no external force exerted thereon.

In addition, material for forming the coil spring 10 is not particularly limited, and, for example, metallic materials such as stainless steel can be used.

As shown in FIG. 12, the cap 9 is composed of a member having a bottomed hollow cylindrical shape. In a mounted state wherein a proximal portion of the cap 9 is mounted to the outer cylinder 2, the cap 9 accommodates (covers) the cover member 7A as a whole. This ensures that in the mounted state, a pushing force is securely prevented from being inadvertently exerted on the cover member 7A. Therefore, inadvertent movement of the cover member 7A from the first position to the second position can be securely prevented from occurring to expose the needlepoint 51, so that mispuncture with the needlepoint 51 is assuredly prevented from occurring. Thus, the cap 9 has the function as exposure prevention means for inhibiting inadvertent exposure of the needlepoint 51 from occurring in the mounted state.

As shown in FIG. 12, the outer cylinder 2 is provided with a ring member 28 at its outer peripheral portion 213, either integrally or in a linked fashion. An outer peripheral portion 281 of the ring member 28 is fitted in a proximal inner peripheral portion 91 of the cap 9 in the mounted state. Such a fitting structure maintains the mounted state securely. Specifically, such a fitting structure prevents assuredly the cap 9 from being easily disengaged from the outer cylinder 2.

As shown in FIG. 19, the ring member 28 is provided with a cam groove 282 in its outer peripheral portion 281. The cam groove 282 is L-shaped in plan view. The cam groove 282 can be divided into a first groove 283 formed along the circumferential direction of the outer peripheral portion 281 of the ring member 28, and a second groove 284 formed along the axial direction. The first groove 283 and the second groove 284 communicate with each other.

As shown in FIG. 18, at the proximal inner peripheral portion 91 of the cap 9, a projected part (cam follower) 92 is formed. In the mounted state, the projected part 92 is engaged with the cam groove 282. With the projected part 92 guided by the first groove 283 of the cam groove 282, the cap 9 is restrained from movement along the axial direction, and can only be turned about the axis. In addition, when the projected part 92 is brought from the first groove 283 into the second groove 284 and guided by the second groove 284, the cap 9 is restrained from turning about the axis, and can only be moved along the axial direction (in the distal direction).

As shown in FIG. 12, in the mounted state, a proximal outer peripheral portion 626 of the cylindrical part 62 of the support member 6A is fitted in the proximal inner peripheral portion 91 of the cap 9. By this fitting structure, the cap 9 in the mounted state is so connected (supported) as to be capable of rotating the support member 6A. Further, the proximal outer peripheral portion 626 of the support member 6A is formed with an elongated ridge 627 along the axial direction (see FIG. 19). The proximal inner peripheral portion 91 of the cap 9 is formed with a groove 93 along the axial direction (see FIGS. 18 and 19). The elongated ridge 627 is inserted in the groove 93. This ensures that the cap 9 in the mounted state is so connected as to be capable of securely rotating the support member 6A.

Such a connection ensures that when the cap 9 is rotated, the rotating force is transmitted from the groove 93 through the elongated ridge 627 to the support member 6A, whereby the support member 6A is rotated. Consequently, the communicating state and the blocked state can be selected assuredly.

In the drug solution injector 1A, while the projected part 92 of the cap 9 in the mounted state is moving in the first groove 283 of the cam groove 282, the support member 6A is rotated as above-mentioned, but the second flow channel 612 of the junction flow channel 61 does not come to face the flow channel 23 in the outer cylinder 2, so that the blocked state is maintained. When the projected part 92 is brought from the first groove 283 into the second groove 284, the support member 6A is further rotated, with the result that the second flow channel 612 of the junction flow channel 61 faces the flow channel 23 in the outer cylinder 2. That is, the communicating state is realized. The junction flow channel 61, the flow channel 23, the cam groove 282, and the projected part 92 are respectively so formed as to attain the above-mentioned configuration.

Further, when the projected part 92 is brought into the second groove 284 (when the communicating state is obtained), it becomes possible to move the cap 9 in the distal direction and thereby to disengage the cap 9. In this case, the projected part 92 of the cap 9 is guided by the second groove 284, and the groove 93 is guided by the elongated ridge 627 of the support member 6A. Accordingly, the cap 9 can be moved smoothly, and the disengaging operation can be performed easily.

Incidentally, at the time of rotating the support member 6A, the operation can be carried out easily by gripping an outer peripheral portion of the cap 9. Thus, the outer peripheral portion of the cap 9 functions as a grip part.

Material for forming the cap 9 is not particularly limited, and, for example, the same materials as those described about the outer cylinder 2 in the first embodiment above can be used.

Now, an example of the method for using the drug solution injector 1A will be described below.

[1] First, the drug solution injector 1A preliminarily filled with the drug solution Q in a sufficient amount for administration into a living body is prepared (see FIG. 12). The drug solution injector 1A is an unused one, wherein the cover member 7A is in the first position. In addition, the cap 9 is mounted, and the cap 9 prevents the cover member 7A from being moved. As a result, the needlepoint 51 is securely prevented from being exposed, so that mispuncture with the needlepoint 51 is assuredly prevented from occurring.

Further, in the drug solution injector 1A, as above-mentioned, the second flow channel 612 of the junction flow channel 61 is closed with the packing 22 of the outer cylinder 2. Therefore, communication between the space 24 inside the outer cylinder 2 and the lumen 52 of the needle tube 5 through the junction flow channel 61 is blocked. As a result, even if a force for pushing the plunger 4 is exerted inadvertently, inadvertent flow-out of the drug solution Q through the needle tube 5 is securely prevented, and, therefore, the drug liquid Q is prevented from being lost uselessly. In addition, since liquid-tightness of the space 24 inside the outer cylinder 2 is maintained, a sterilized state of the drug solution Q is maintained.

In addition, the projected part 92 of the cap 9 is located at an end portion 283a, on the opposite side from the second groove 284 (on the lower side in FIG. 19), of the first groove 283 in the outer cylinder 2.

Figure 13:
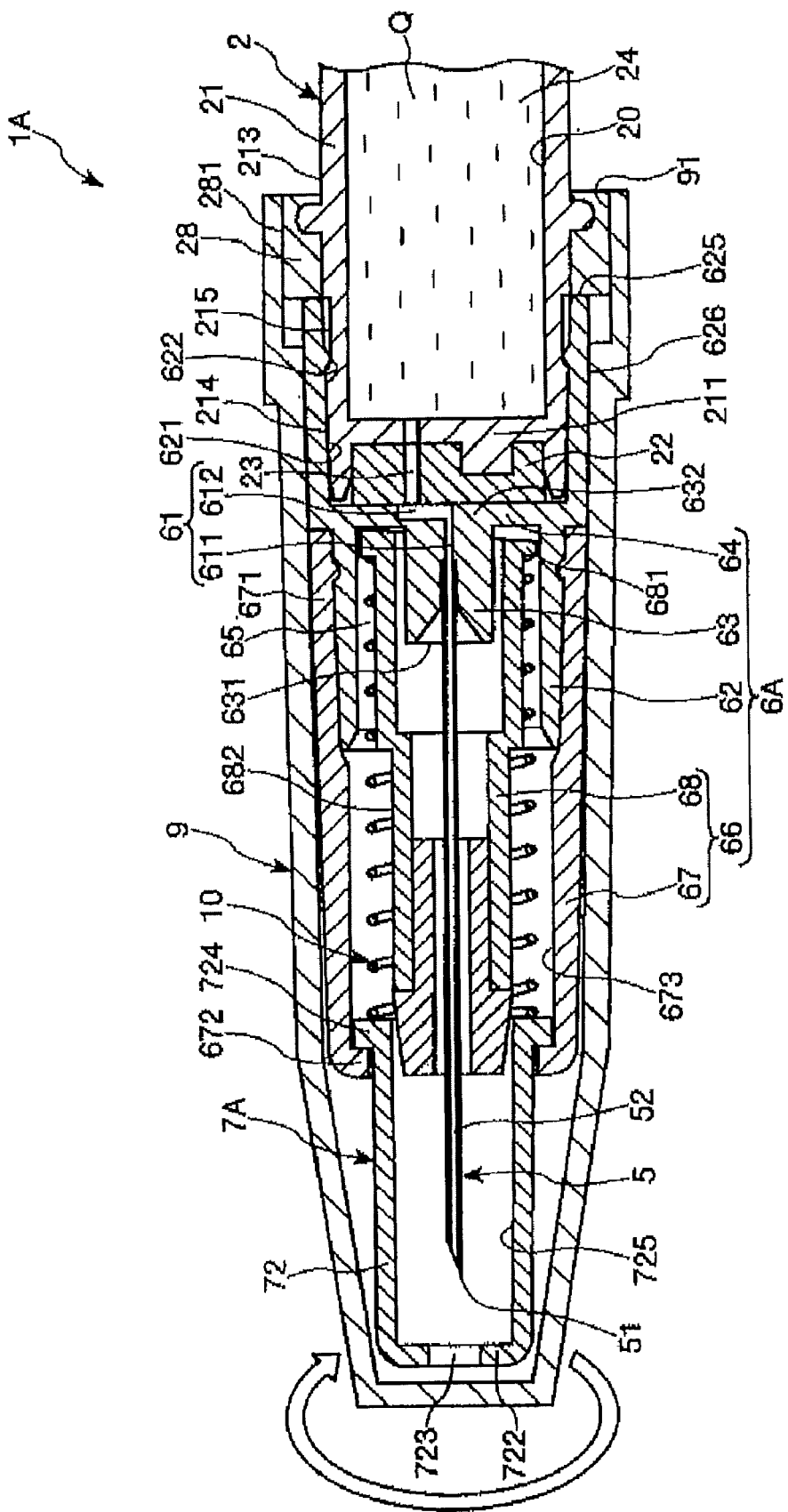
FIG. 13 is a longitudinal sectional view for sequentially illustrating the states in use of the drug solution injector (second embodiment) of the present invention.

[2] Next, the cap 9 is gripped and rotated in the direction of arrow in FIG. 13 starting from the state shown in FIG. 12. This rotating operation is performed smoothly, with the projected part 92 of the cap 9 sliding in the first groove 283 in the outer cylinder 2 as above-mentioned. In addition, even if it is attempted to pull the cap 9 in the distal direction during this rotating operation, the pulling operation can be prevented from occurring, since the projected part 92 of the cap 9 abuts on an edge portion of the first groove 283 in the outer cylinder 2. This prevents the cap 9 from being detached inadvertently. Further, as above-mentioned, the blocked state is maintained during the rotating operation.

Then, simultaneously when the projected part 92 of the cap 9 reaches (enters into) the second groove 284 from the first groove 283 in the outer cylinder 2, the second flow channel 612 of the junction flow channel 61 is displaced to the position for opening toward the flow channel 23 in the outer cylinder 2, whereby the space 24 inside the outer cylinder 2 and the lumen 52 of the needle tube 5 communicate with each other through the junction flow channel 61. This communicating state is maintained until the drug solution Q is administered into a living body (see FIG. 13). Thus, in the drug solution injector 1A, when the projected part 92 of the cap 9 reaches the second groove 284 from the first groove 283 in the outer cylinder 2, rotation of the cap 9 is restrained. Thus, it can be realized that the drug solution injector 1A has been put into the communicating state.

[3] Subsequently, as shown in FIG. 14, the cap 9 is pulled in the direction of arrow in the figure. By this, the cap 9 can be detached. This detaching operation is carried out smoothly, since the projected part 92 of the cap 9 slides in the second groove 284 in the outer cylinder 2 as above-mentioned.

[4] Next, by gripping the outer cylinder 2, the bottom portion 722 of the cover member 7A is pressed against a puncture part (target part) of a living body surface 200 against the biasing force of the coil spring 10, thereby moving the cover member 7A into the second position (see FIG. 15). Consequently, the needlepoint 51 of the needle tube 5 having been covered with the cover member 7A is protruded in the distal direction through the through-hole 723 in the cover member 7A, to puncture the body surface 200 (see FIG. 15).

[5] Subsequently, while maintaining the state shown in FIG. 15, an index finger and a middle finger having been gripping the outer cylinder 2 are put on an edge portion of the flange 25 of the outer cylinder 2, and a thumb is put on the finger holding part 42 of the plunger 4. Then, the finger holding part 42 is pushed in the distal direction by the thumb (see FIG. 16). By this operation, the gasket 3 is moved in the distal direction, and, therefore, the drug solution Q in the space 24 inside the outer cylinder 2 is reliably administered (injected) into the living body by sequentially passing through the flow channel 23 in the outer cylinder 2, the junction flow channel 61 in the support member 6A, and the lumen 52 of the needle tube.

[6] After the administration of the drug solution Q, the drug solution injector 1A (cover member 7A) is separated from the body surface 200. In this instance, the cover member 7A is pushed in the distal direction by the restoring force of the coil spring 10, to be returned into the first position (see FIG. 17). As a result, the needle tube 5 is again covered up to its needlepoint 51. Therefore, scattering of blood in contact with the needlepoint 51 or mispuncture with the needlepoint 51 carrying the blood in contact therewith can be prevented from occurring, so that infection with the blood can be prevented from occurring.

Incidentally, in the drug solution injector 1A (operation mechanism), one of the cover member 7A and the cap 9 can be omitted.

In addition, in this embodiment, of the proximal inner peripheral portion 91 of the cap 9 and the outer peripheral portion 281 of the ring member 28 (outer cylinder 2), the outer peripheral portion 281 of the ring member 28 is formed with the cam groove 282, whereas the proximal inner peripheral portion 91 of the cap 9 is formed with the projected part 92. However, this configuration is not limitative. For example, a configuration may be adopted in which the outer peripheral portion 281 of the ring member 28 is provided with a projected part like the projected part 92 whereas the proximal inner peripheral portion 91 of the cap 9 is provided with a cam groove like the cam groove 282.

Further, of the proximal inner peripheral portion 91 of the cap 9 and the proximal outer peripheral portion 626 of the support member 6A, the proximal outer peripheral portion 626 of the support member 6A is formed with the elongated ridge 627 whereas the proximal inner peripheral portion 91 of the cap 9 is formed with the groove 93. However, this configuration is not limitative. A configuration may be adopted in which the proximal outer peripheral portion 626 of the support member 6A is provided with a groove like the groove 93 whereas the proximal inner peripheral portion 91 of the cap 9 is provided with an elongated ridge like the elongated ridge 627.

Third Embodiment

Figure 20:
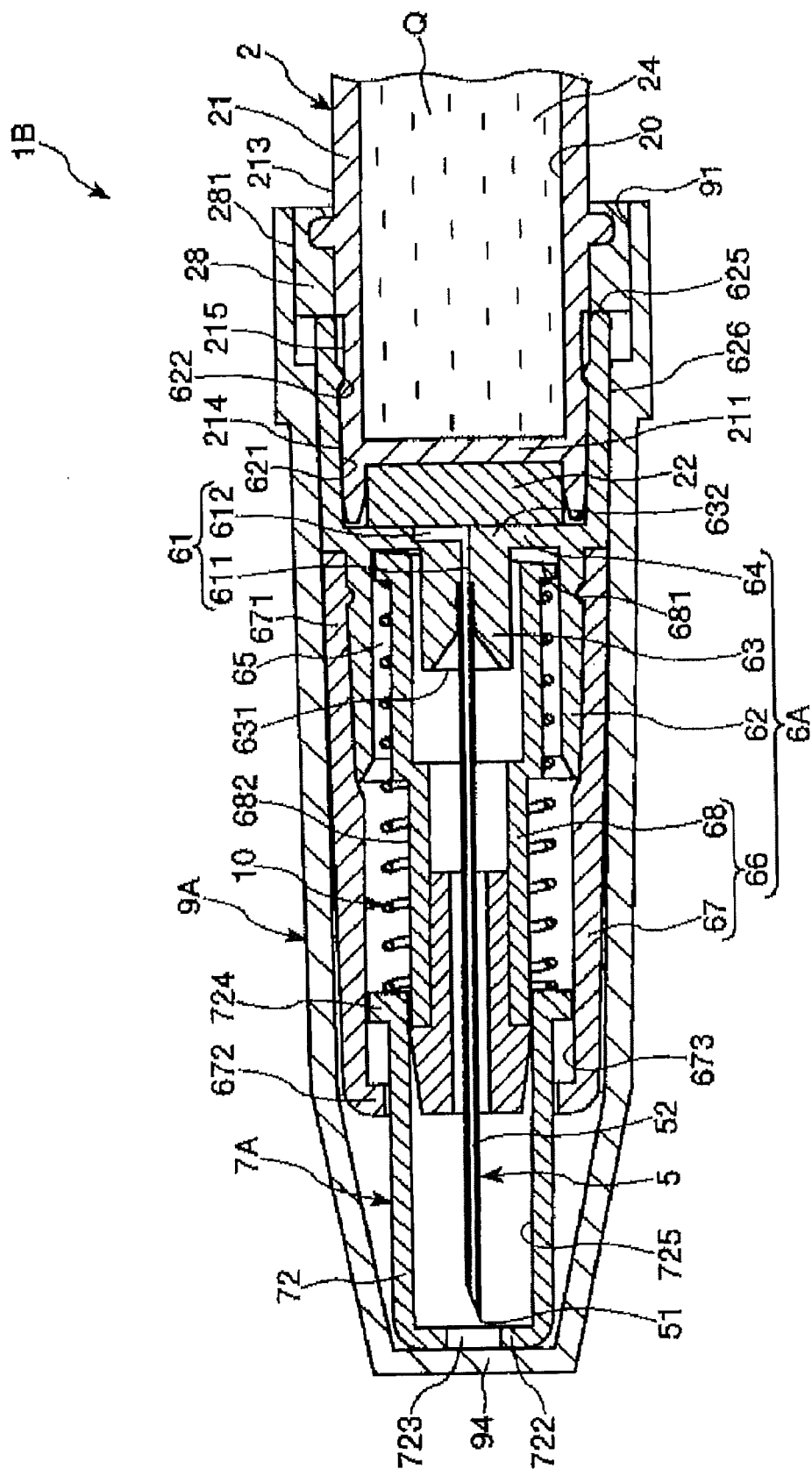
FIG. 20 is a longitudinal sectional view for sequentially illustrating the states in use of a drug solution injector (third embodiment) of the present invention.
Figure 21:
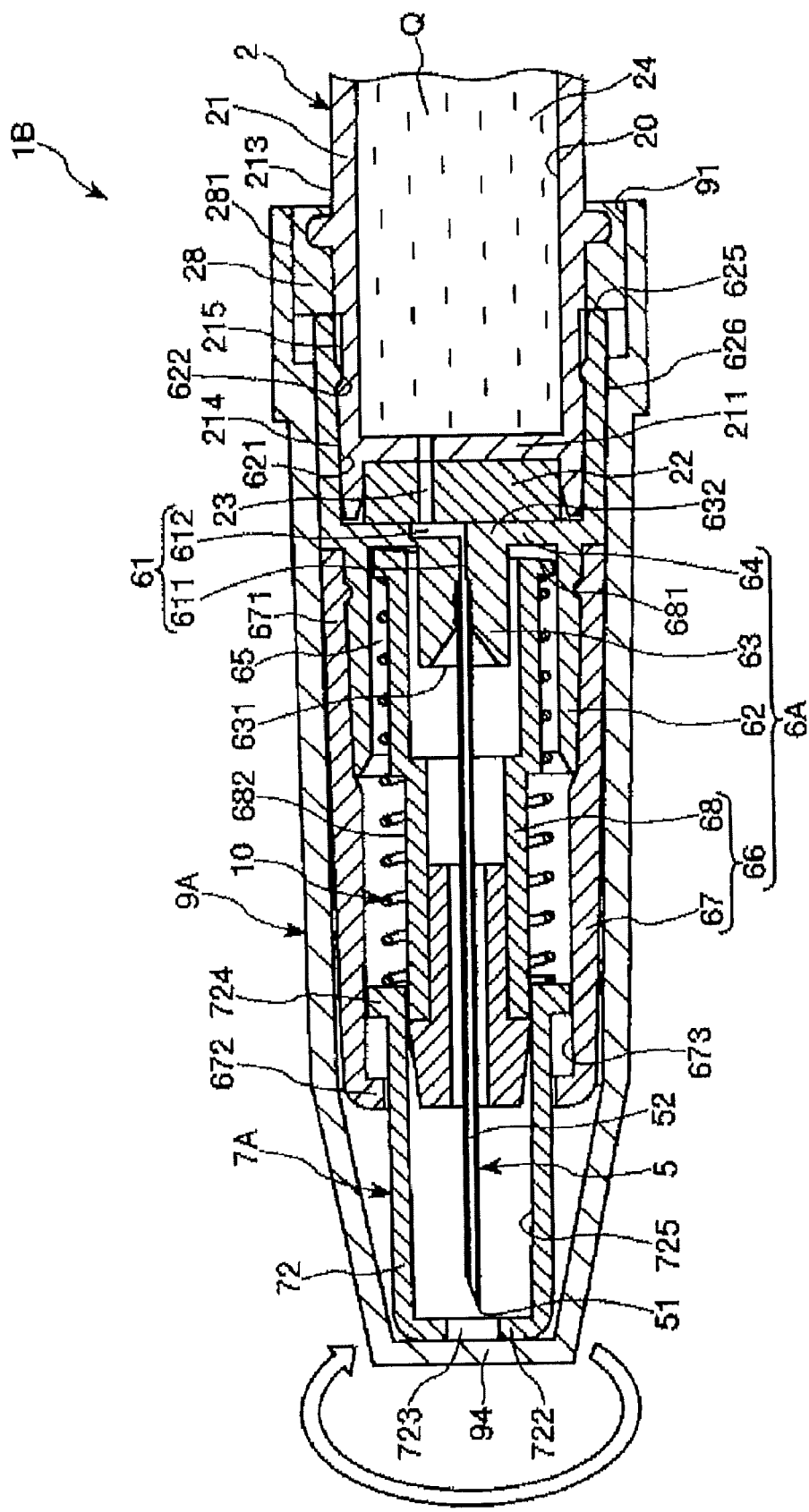
FIG. 21 is a longitudinal sectional view for sequentially illustrating the states in use of the drug solution injector (third embodiment) of the present invention.
Figure 22:
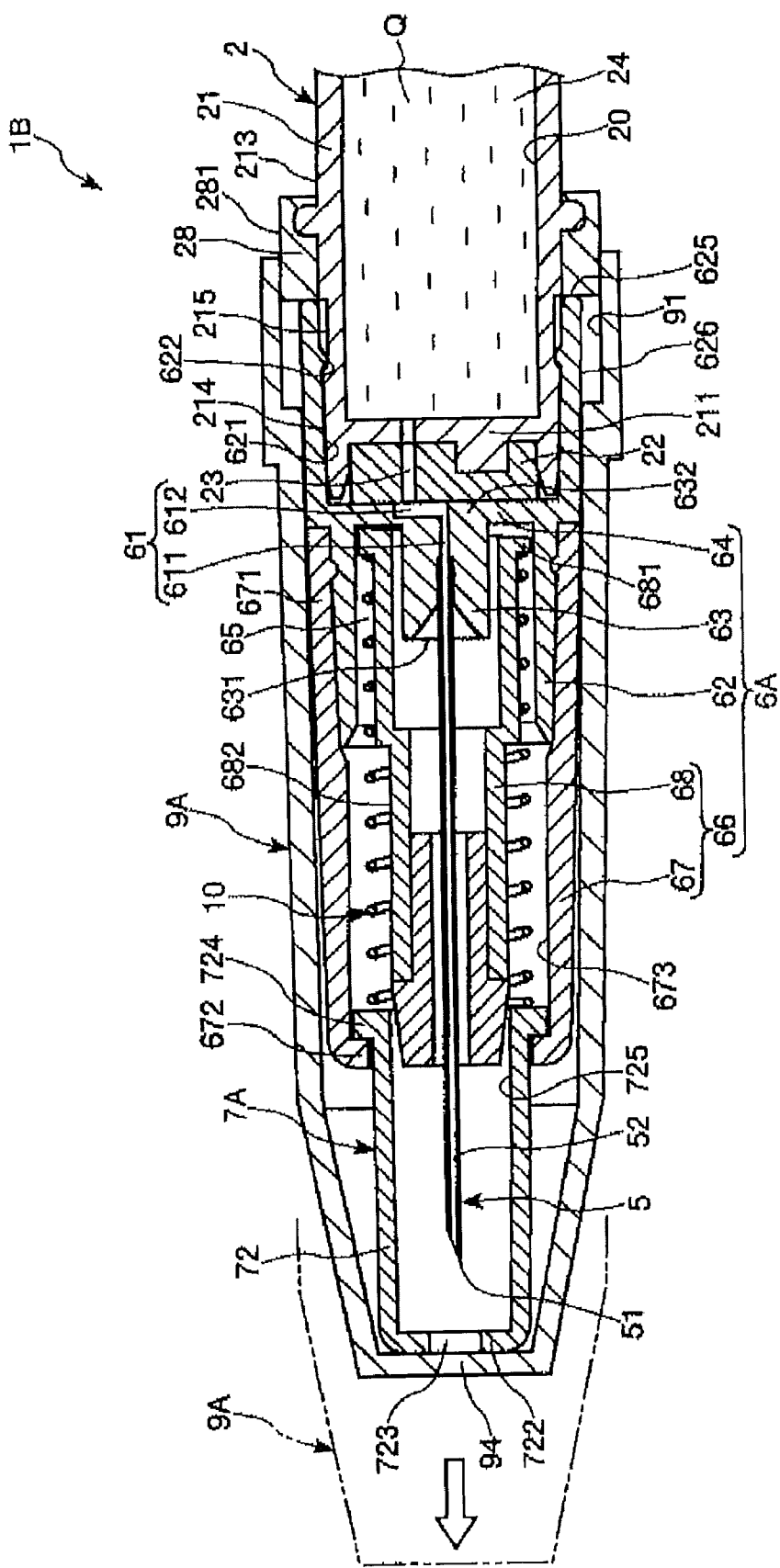
FIG. 22 is a longitudinal sectional view for sequentially illustrating the states in use of the drug solution injector (third embodiment) of the present invention.

FIGS. 20 to 22 are longitudinal sectional views for sequentially illustrating the states in use of a drug solution injector (third embodiment) of the present invention. Incidentally, in the following, for convenience of description, the right side in FIGS. 20 to 22 will be referred to as "proximal", and the left side as "distal".

Now, a third embodiment of the drug solution injector according to the present invention will be described referring to these drawings. The following description will be centered on differences from the above-described embodiments, and descriptions of the same items as above will be omitted.

This embodiment is the same as the second embodiment above, except for difference in the length of the cap.

In a drug solution injector 1B shown in FIGS. 20 to 22, a cap 9A has a length which is shorter than that of the cap 9 of the drug solution injector 1A in the second embodiment above. By this configuration, the overall length of the drug solution injector 1B can be made shorter than that of the drug solution injector 1A, and, therefore, the drug solution injector 1B can be made smaller in size.

In addition, since the cap 9A has the reduced length, in the mounted state of the cap 9A, its top part (distal wall portion (abutment part)) 94 is in abutment on a bottom portion 722 of a cover member 7A biased in the distal direction by a biasing force of a coil spring 10 (see FIG. 20). Through the cover member 7A, the cap 9A is also biased in the distal direction by the biasing force of the coil spring 10.

In the drug solution injector 1B in such a state (the state shown in FIG. 20), when the cap 9A is gripped and rotated in the direction of arrow in FIG. 21, a communicating state (the state shown in FIG. 21) is obtained, as above-mentioned. Further, when the communicating state is obtained, a projected part 92 of the cap 9 is located in a second groove 284 in an outer cylinder 2. Therefore, restraint on movement of the cap 9 in the distal direction is released, so that the cap 9A is instantaneously biased (pushed out) in the distal direction by the biasing force of the coil spring 10 through the cover member 7A (see FIG. 22). This enables the cap 9A to be detached easily (see the cap 9A indicated by two-dotted chain line in FIG. 22). Thus, in the drug solution injector 1B, at the time of detaching the cap 9A, the biasing force of the coil spring 10 functions as a force for assisting the detaching operation.

While the drug solution injector according to the present invention has been described above by way of the embodiments thereof shown in the drawings, the present invention is not limited to the embodiments. Components of the drug solution injector can be replaced by those of arbitrary configurations that can exhibit the same or equivalent functions to the original ones. Further, arbitrary structures may be added.

In addition, the drug solution injector according to the present invention may be an arbitrary combination of two or more configurations (features) extracted from among the above-described embodiments.

For instance, the drug solution injectors according to the second embodiment and the third embodiment may have reprotrusion prevention means similar to the prevention means of the drug solution injector according to the first embodiment.

Further, while the turning angle of the support member is set at 90° in the embodiments above, this setting is not limitative, and the turning angle may be set, for example, at 30°, 45°, or 180°.

INDUSTRIAL APPLICABILITY

A drug solution injector according to the present invention includes: a needle tube having a sharp needlepoint at a distal end thereof; an outer cylinder having a bottomed hollow cylindrical shape, the outer cylinder being located on a proximal side of the needle tube and having an inside space that can communicate with an inside of the needle tube; a gasket slidable within the outer cylinder; a drug solution contained in a space surrounded by the outer cylinder and the gasket; a support member which supports the needle tube and has a flow channel having a distal end capable of communicating with the inside of the needle tube and a proximal end capable of communicating with an inside of the outer cylinder; an operation mechanism having a part of covering at least the needlepoint of the needle tube and performing selection between a communicating state wherein the inside of the needle tube and the inside of the outer cylinder communicate with each other through the flow channel and a blocked state wherein the communication is blocked, by rotating the support member; and exposure prevention means for preventing exposure of the needlepoint. Therefore, by the exposure prevention means, the needlepoint of the needle tube can be securely prevented from being exposed inadvertently. This ensures that mispuncture with the needlepoint is prevented more assuredly. In addition, the communicating state and the blocked state can be selected by the operation mechanism. With the drug solution injector set into the blocked state, the drug solution in the outer cylinder can be securely prevented from being inadvertently caused to flow out through the needle tube, and therefore, the drug solution can be prevented from being lost uselessly. Accordingly, the drug solution injector of the present invention has industrial applicability.

The invention claimed is:

1. A drug solution injector comprising:
    a needle tube having a sharp needlepoint at a distal end thereof;
    an outer cylinder having a bottomed hollow cylindrical shape, the outer cylinder being located on a proximal side of the needle tube and having an inside space that can communicate with an inside of the needle tube;
    a gasket slidable within the outer cylinder;
    a drug solution contained in a space surrounded by the outer cylinder and the gasket;
    a support member which supports the needle tube and has a flow channel having a distal end capable of communicating with the inside of the needle tube and a proximal end capable of communicating with an inside of the outer cylinder;
    an operation mechanism which is fixed in a state of covering at least the needlepoint of the needle tube and performs selection between a communicating state wherein the inside of the needle tube and the inside of the outer cylinder communicate with each other through the flow channel and a blocked state wherein the communication is blocked, by rotating the support member; and
    exposure prevention means for preventing exposure of the needlepoint.

2. The drug solution injector according to claim 1, wherein the operation mechanism is composed of a cover member supported by the support member so as to be displaceable to a first position for covering the needle tube up to the needlepoint, and to a second position for exposing the needlepoint through movement from the first position toward the proximal end, and the support member is rotated when the cover member is in the first position.

3. The drug solution injector according to claim 2,
    wherein the support member supports the cover member so that the cover member is rotatable around an axis of the outer cylinder and that the cover member is movable along the axial direction of the outer cylinder, and
    the proximal end of the flow channel is closed by a bottom portion of the outer cylinder to attain the blocked state when the cover member is in the first position, turning of the cover member in the first position around the axis of the outer cylinder releases the restraint on the cover member by the exposure prevention means and causes the proximal end of the flow channel to face the inside of the outer cylinder to attain the communicating state, and movement of the cover member from the first position to the second position in this communicating state causes the needlepoint to protrude from the cover member.

4. The drug solution injector according to claim 2, wherein the exposure prevention means restrains the cover member from moving from the first position to the second position.

5. The drug solution injector according to claim 4,
    wherein the cover member has a hollow cylindrical shape and has a tongue piece protruding in the proximal direction, and
    the exposure prevention means is composed of a projected part formed on an outer peripheral portion of the outer cylinder, and restrains movement of the cover member in the proximal direction through abutment of a proximal portion of the tongue piece on a distal portion of the projected part.

6. The drug solution injector according to claim 2,
wherein the support member and the cover member have respective hollow cylindrical portions, and constitute a fitting structure in which an inner outer peripheral portion of the cover member is fitted to an inner peripheral portion of the support member, and one of the outer peripheral portion of the support member and the inner peripheral portion of the cover member is formed with an elongated ridge along the axial direction of the outer cylinder, whereas the other is inserted by the elongated ridge and formed with a groove for guiding the elongated ridge.

7. The drug solution injector according to claim 1, wherein the operation mechanism is composed of at least one of two members including a cover member that is supported by the support member so as to be displaceable to a first position for covering the needle tube up to the needlepoint, and to a second position for exposing the needlepoint through movement from the first position in the proximal direction, and a cap which is detachably mounted on the outer cylinder, is connected so as to be capable of rotating the support member in a mounted state, and covers the needle tube up to the needlepoint.

8. The drug solution injector according to claim 1, wherein the operation mechanism is composed of a cover member that is supported by the support member so as to be displaceable to a first position for covering the needle tube up to the needlepoint, and to a second position for exposing the needlepoint through movement from the first position in the proximal direction, and a cap which is detachably mounted on the outer cylinder, is connected so as to be capable of rotating the support member in a mounted state, and accommodates the cover member entirely therein.

9. The drug solution injector according to claim 7,
wherein the support member supports the cap so that the cap is rotatable around the axis of the outer cylinder and supports the cap so that the cap is movable along the axial direction of the outer cylinder, and the proximal end of the flow channel is closed by a bottom portion of the outer cylinder in the blocked state, and turning of the cap around the axis of the outer cylinder from the blocked state causes the proximal end of the flow channel to face the inside of the outer cylinder to attain the communicating state, in which the cap can be disengaged through movement in the distal direction.

10. The drug solution injector according to claim 9,
wherein the cap has a hollow cylindrical portion, and constitutes a fitting structure in which an outer peripheral portion of the outer cylinder is fitted in an inner peripheral portion of the cylindrical portion, and one of the inner peripheral portion of the cap and the outer peripheral portion of the outer cylinder is provided at least with a cam groove formed along the axial direction thereof, whereas the other is provided with a projected part which is engaged with and guided by the cam groove.

11. The drug solution injector according to claim 7, wherein in the mounted state, the cap constitutes a part of the exposure prevention means.

12. The drug solution injector according to claim 11, wherein an operation of moving the cover member can be performed in a disengaged state where the cap has been disengaged.

13. The drug solution injector according to claim 7,
wherein the support member and the cap each have hollow cylindrical portions, and constitute a fitting structure wherein an outer peripheral portion of the support member is fitted in an inner peripheral portion of the cap, and one of the inner peripheral portion of the cap and the outer peripheral portion of the support member is formed with an elongated ridge along the axial direction of the outer cylinder, whereas the other is formed with a groove in which the elongated ridge is inserted.

14. The drug solution injector according to claim 8, wherein the operation mechanism has a biasing member for biasing the cover member in the distal direction.

15. The drug solution injector according to claim 14, wherein the cap has a contact part with which the cover member biased in the distal direction by a biasing force of the biasing member makes contact.

16. The drug solution injector according to claim 15, wherein the cap is biased in the distal direction by a biasing force of the biasing member through the cover member in the mounted state, and the biasing force assists disengagement of the cap when the cap is disengaged.

17. The drug solution injector according to claim 2, wherein the cover member has a bottomed hollow cylindrical shape, and a through-hole through which the needle tube can be passed is formed in a bottom portion of the cover member.

18. The drug solution injector according to claim 2, wherein when the cover member is moved from the second position to the first position, the needle tube is again covered up to the needlepoint by the cover member disposed in the first position.

19. The drug solution injector according to claim 2, comprising reprotrusion prevention means for preventing the needlepoint once protruded and retracted in relation to the cover member from again protruding from the cover member.

20. The drug solution injector according to claim 19,
wherein the reprotrusion preventing means comprises an inhibiting member which is disengageably mounted to the support member and which is clamped between the support member and the cover member when disengaged from the support member so as to inhibit the cover member from again moving to the second position, a biasing member for biasing the inhibiting member in the distal direction, and a lock part which is provided on the cover member and which locks the inhibiting member against a biasing force of the biasing member, and the inhibiting member is released from the locking by the lock part, so as to be disengageable from the support member by the biasing force of the biasing member, when the cover member moves from the first position to the second position.

21. The drug solution injector according to claim 8,
wherein the support member supports the cap so that the cap is rotatable around the axis of the outer cylinder and supports the cap so that the cap is movable along the axial direction of the outer cylinder, and the proximal end of the flow channel is closed by a bottom portion of the outer cylinder in the blocked state, and turning of the cap around the axis of the outer cylinder from the blocked state causes the proximal end of the flow channel to face the inside of the outer cylinder to attain the communicating state, in which the cap can be disengaged through movement in the distal direction.

22. The drug solution injector according to claim 8, wherein in the mounted state, the cap constitutes a part of the exposure prevention means.

23. The drug solution injector according to claim 8,
wherein the support member and the cap each have hollow cylindrical portions, and constitute a fitting structure wherein an outer peripheral portion of the support member is fitted in an inner peripheral portion of the cap, and one of the inner peripheral portion of the cap and the outer peripheral portion of the support member is formed with an elongated ridge along the axial direction of the outer cylinder, whereas the other is formed with a groove in which the elongated ridge is inserted.

24. The drug solution injector according to claim 7, wherein the cover member has a bottomed hollow cylindrical shape, and a through-hole through which the needle tube can be passed is formed in a bottom portion of the cover member.

25. The drug solution injector according to claim 8, wherein the cover member has a bottomed hollow cylindrical shape, and a through-hole through which the needle tube can be passed is formed in a bottom portion of the cover member.

26. The drug solution injector according to claim 7, wherein when the cover member is moved from the second position to the first position, the needle tube is again covered up to the needlepoint by the cover member disposed in the first position.

27. The drug solution injector according to claim 8, wherein when the cover member is moved from the second position to the first position, the needle tube is again covered up to the needlepoint by the cover member disposed in the first position.

28. The drug solution injector according to claim 7, comprising reprotrusion prevention means for preventing the needlepoint once protruded and retracted in relation to the cover member from again protruding from the cover member.

29. The drug solution injector according to claim 8, comprising reprotrusion prevention means for preventing the needlepoint once protruded and retracted in relation to the cover member from again protruding from the cover member.

* * * * *